(12) United States Patent
Muramatsu et al.

(10) Patent No.: US 7,495,597 B2
(45) Date of Patent: *Feb. 24, 2009

(54) COUNTER CIRCUIT, AD CONVERSION METHOD, AD CONVERTER, SEMICONDUCTOR DEVICE FOR DETECTING DISTRIBUTION OF PHYSICAL QUANTITIES, AND ELECTRONIC APPARATUS

(75) Inventors: Yohinori Muramatsu, Kanagawa (JP); Noriyuki Fukushima, Kanagawa (JP); Yoshikazu Nitta, Tokyo (JP); Yukihiro Yasui, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/862,364

(22) Filed: Sep. 27, 2007

(65) Prior Publication Data
US 2008/0019472 A1    Jan. 24, 2008

Related U.S. Application Data

(63) Continuation of application No. 11/113,949, filed on Apr. 25, 2005, now Pat. No. 7,292,177.

(30) Foreign Application Priority Data
Apr. 26, 2004  (JP) ............................ 2004-129389

(51) Int. Cl.
*H03M 1/34*    (2006.01)
(52) U.S. Cl. .................. 341/164; 341/155; 377/45; 377/107; 377/110
(58) Field of Classification Search .............. 341/164; 377/45
See application file for complete search history.

(56) References Cited

U.S. PATENT DOCUMENTS
4,023,160 A    5/1977    Kirschner
(Continued)

FOREIGN PATENT DOCUMENTS
EP    1566891    8/2005
(Continued)

OTHER PUBLICATIONS
Database WPI; Section EI, Week 199330; Derwent Publications Ltd., London, GB; AN 1993-241486 XP002367192.
(Continued)

*Primary Examiner*—Khai M Nguyen
(74) *Attorney, Agent, or Firm*—Sonnenschein Nath & Rosenthal LLP

(57) ABSTRACT

An asynchronous counter that is capable of switching count mode includes flip-flops, and three-input single-output tri-value switches respectively provided between the adjacent pairs of the flip-flops. The tri-value switches switch among three values, namely, non-inverting outputs and inverting outputs of the flip-flops and a power supply level. Each of the tri-value switches switch among the three input signals according to two-bit control signals, and input a selected signal to a clock terminal of a subsequent flip-flop. When count mode is switched according to the control signals, a count value immediately before the mode switching is set as an initial value, and counting after the mode switching is started from the initial value.

12 Claims, 23 Drawing Sheets

U.S. PATENT DOCUMENTS

| | | | | |
|---|---|---|---|---|
| 4,509,183 | A | * | 4/1985 | Wright .................. 377/125 |
| 5,877,715 | A | | 3/1999 | Gowda et al. |
| 6,567,340 | B1 | | 5/2003 | Nataraj et al. |
| 6,735,270 | B1 | * | 5/2004 | Yeung ..................... 377/34 |
| 7,292,177 | B2 | * | 11/2007 | Muramatsu et al. ...... 341/164 |

FOREIGN PATENT DOCUMENTS

| | | |
|---|---|---|
| EP | 1 592 134 | 11/2005 |
| JP | 61-100025 | 5/1986 |
| JP | 1987 195924 | 8/1987 |
| JP | 1994 311025 | 4/1994 |
| JP | 6-164372 | 6/1994 |
| JP | 1999 017526 | 9/2008 |
| SU | 1750056 | 7/1992 |

OTHER PUBLICATIONS

Stan, Mircea R.; Long and Fast Up/Down Counters; IEEE Transactions on Computers, IEEE Service Center, Los Alamitos, CA, US, vol. 47, No. 7, Jul. 1998, pp. 722-735, XP000782017.

European Search Report dated Feb. 28, 2006.

European Search Report dated May 11, 2006.

Office Action issued on Mar. 11, 2008 in corresponding Japanese Patent Application JP 2004 129389.

* cited by examiner

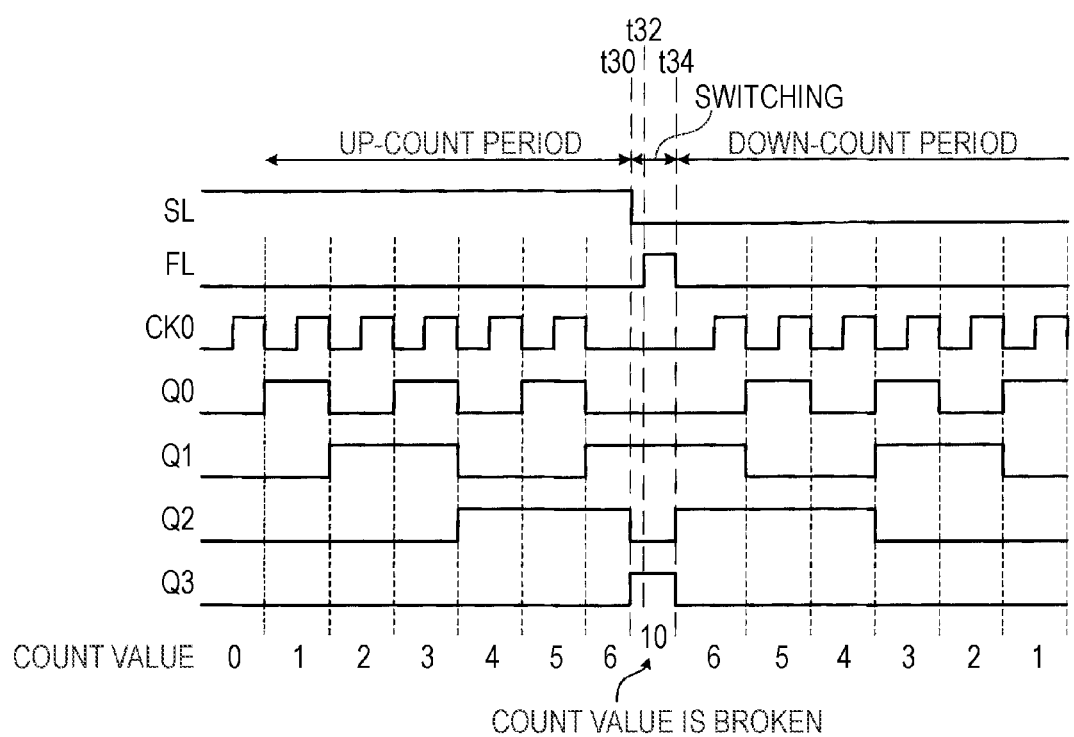

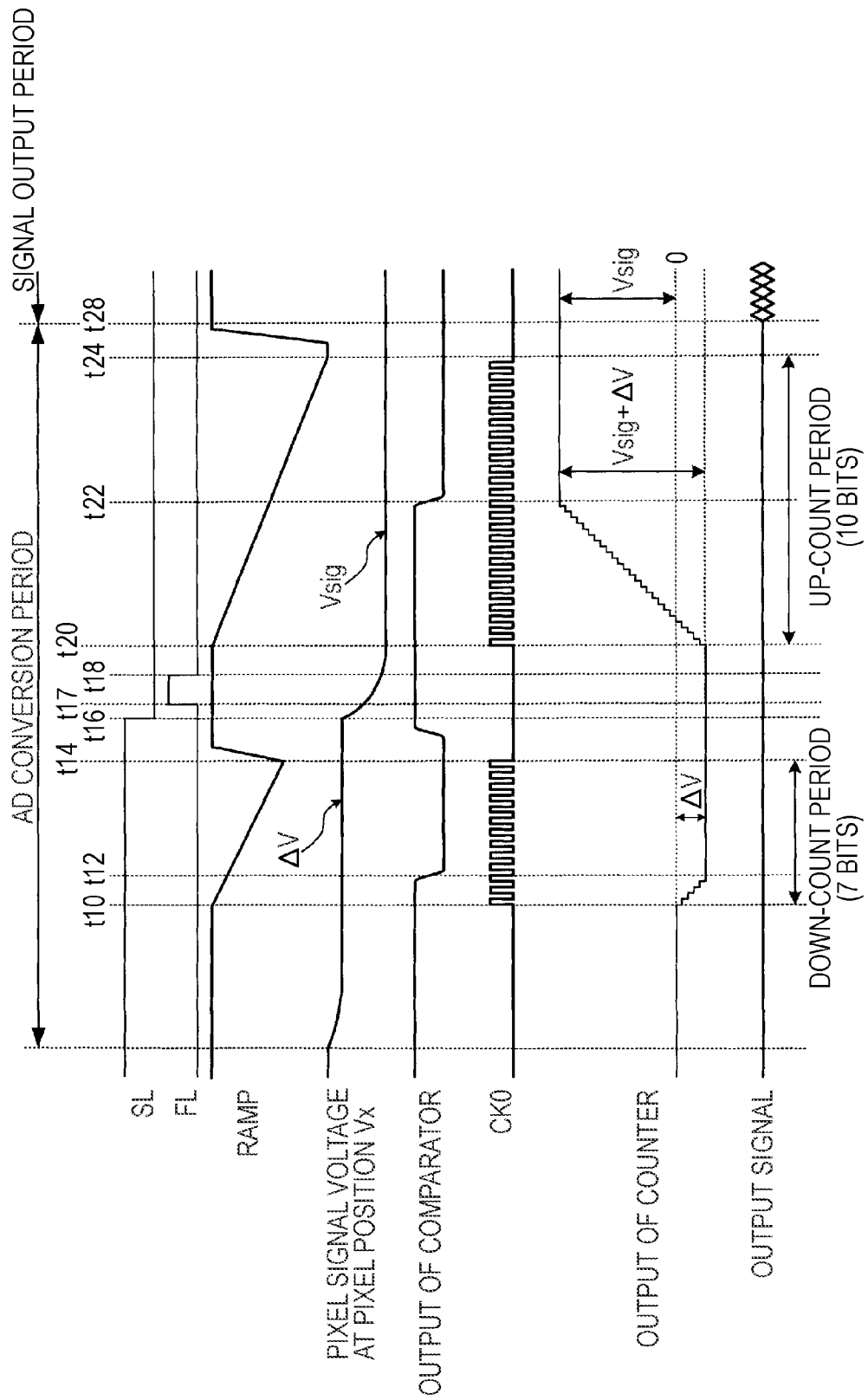

COUNTER CIRCUIT, AD CONVERSION METHOD, AD CONVERTER, SEMICONDUCTOR DEVICE FOR DETECTING DISTRIBUTION OF PHYSICAL QUANTITIES, AND ELECTRONIC APPARATUS

RELATED APPLICATION DATA

This application is a continuation of U.S. patent application Ser. No. 11/113,949, filed Apr. 25, 2005, the entirety of which is incorporated herein by reference to the extent permitted by law. The present invention claims priority to Japanese Patent Application No. 2004-129389 filed in the Japanese Patent Office on Apr. 25, 2004, the entirety of which also is incorporated by reference herein to the extent permitted by law.

BACKGROUND OF THE INVENTION

1. Field of the Invention

The present invention relates to asynchronous counter circuits, analog-to-digital (AD) conversion methods and AD converters for converting analog signals into digital data using the counter circuits, semiconductor devices for detecting distribution of physical quantities by an array of a plurality of unit elements, and electronic apparatuses.

More specifically, the present invention relates to an asynchronous counter and techniques of AD conversion, suitably used in electronic apparatuses, for example, a semiconductor device for detecting distribution of physical quantities, such as a solid-state imaging device, that allows reading electric signals representing distribution of physical quantities obtained by an array of a plurality of unit elements that are sensitive to electromagnetic waves input from the outside, such as light or radiation.

2. Description of the Related Art

Semiconductor devices for detecting physical quantities, including a line or matrix of unit elements that are sensitive to electromagnetic waves input from the outside, such as light or radiation, are used in various fields.

For example, in the field of video apparatuses, charge coupled device (CCD), metal oxide semiconductor (MOS), and complementary metal oxide semiconductor (CMOS) solid-state imaging devices for detecting light (an example of electromagnetic wave) as a physical quantity are used. These devices read distribution of physical quantities in the form of electric signals obtained by unit elements (pixels in the case of a solid-state imaging device).

In a type of solid-state imaging device, referred to as an active pixel sensor (APS) or gain cell, a driving transistor for amplification is provided in a pixel signal generator that generates a pixel signal corresponding to signal charges generated by a charge generator. Many CMOS solid-state imaging devices are of the type described above.

In such an active pixel sensor, in order to read pixel signals to the outside, address control is exercised on a pixel unit including an array of unit pixels so that signals can be read from arbitrarily selected individual unit pixels. That is, an active pixel sensor is an example of address-controlled solid-state imaging device.

For example, in an active pixel sensor, which is a type of X-Y-addressed solid-state imaging device including a matrix of unit pixels, each pixel is implemented using an active element of the MOS structure (MOS transistor) or the like so that the pixel itself is capable of amplification. That is, signal charges (photoelectrons) accumulated in a photodiode that functions as a photoelectric converter are amplified by the active element, and the amplified signals are read as image information.

In this type of X-Y-addressed solid-state imaging device, for example, a pixel unit includes a two-dimensional array of a large number of pixel transistors. Accumulation of signal charges corresponding to incident line is started on a line-by-line basis or pixel-by-pixel basis. Current or voltage signals based on the accumulated signal charges are sequentially read from the respective pixels according to addressing. In the case of MOS (including CMOS) solid-state imaging device, as an example of address control, according to a method that is often used, pixels on one row are simultaneously accessed to read pixel signals from the pixel unit on a row-by-row basis.

The analog pixel signals read from the pixel unit are converted into digital data by an analog-to-digital converter as needed. Since the pixel signals are output with signal components added to reset components, true effective signal components must be extracted by taking difference between signal voltage corresponding to reset component and signal voltage corresponding to signal component.

This also applies to a case where analog pixel signals are converted into digital data. Ultimately, a difference signal component representing a difference between a signal voltage corresponding to a reset component and a signal voltage corresponding to a signal component must be converted into digital data. For this purpose, various schemes for AD conversion have been proposed, for example, as described in W. Yang et. al., "An Integrated 800×600 CMOS Image System," ISSCC Digest of Technical Papers, pp. 304-305, February, 1999 (hereinafter referred to as a first non-patent document), YONEMOTO Kazuya, "CCD/CMOS Imeeji sensa no kiso to ouyou", CQ Publishing Co., Ltd., Aug. 10, 2003, First Edition, pp. 201 to 203 (hereinafter referred to as a second non-patent document), IMAMURA Toshifumi and YAMAMOTO Yoshiko, "3. Kousoku kinou CMOS imeeji sensa no kenkyuu", found on the Internet on Mar. 15, 2004 (hereinafter referred to as a third non-patent document), IMAMURA Toshifumi, YAMAMOTO Yoshiko, and HASEGAWA Naoya, "3. Kousoku kinou CMOS imeeji sensa no kenkyuu", found on the Internet on Mar. 15, 2004 (hereinafter referred to as a fourth non-patent document), Oh-Bong Kwon et. al., "A Novel Double Slope Analog-to-Digital Converter for a High-Quality 640×480 CMOS Imaging System", VL3-03, 1999, IEEE, pp. 335 to 338 (hereinafter referred to as a fifth non-patent document), and Japanese Unexamined Patent Application Publication No. 11-331883 (hereinafter referred to as a first patent document).

According to the schemes of AD conversion described in the first to fifth non-patent documents and the first patent document, AD conversion is performed using a counter circuit. The counter circuit used is usually a synchronous counter in which a flip-flop (basic element of the counter) outputs a count value in synchronization with a counter clock.

In the case of a synchronous counter, however, the operations of all the flip-flops are restricted by the count clock, which is problematic when an operation at a higher frequency is needed.

It is also possible to use an asynchronous counter as a counter circuit, as described, for example, in the fourth and fifth non-patent documents. An asynchronous counter is suitable for high-speed operation since the limiting operation frequency thereof is determined only by the limiting frequency of the first flip-flop. Thus, an asynchronous counter is preferably used as a counter circuit when an operation at a higher frequency is needed.

FIG. 18 is a diagram showing an asynchronous counter according to the related art, which is capable of switching mode. A counter circuit 900 is capable of functioning as a 4-bit asynchronous counter. For example, the counter circuit 900 is implemented by cascade connection of a plurality of negative-edge D flip-flops 912, 914, 916, and 918 (collectively 910). Each of the flip-flops 910 has an inverting output NQ (indicated with a horizontal bar over Q) connected to a D input terminal thereof. A clock terminal CK of the first flip-flop 910 receives input of a count clock CK0.

Furthermore, the counter circuit 900 includes two-input single-output switches 922, 924, and 926 (collectively 920) for switching the values of the non-inverting outputs Q and the inverting outputs NQ of the flip-flops 910 respectively between the adjacent pairs of the flip-flops 910. Each of the switches 920 switches the two input signals according to a control signal SW from a controller (not shown) and inputs a selected signal to the clock terminal CK of the subsequent flip-flop 910.

The control signal SW is used to switch counting operation of the counter circuit 900 between up-counting and down-counting. When the control signal is at High (H) level, the non-inverting output Q is selected so that the counter circuit 900 enters an up-count mode. On the other hand, when the control signal SW is at Low (L) level, the inverting output NQ is selected so that the counter circuit 900 enters a down-count mode.

In the conventional asynchronous counter shown in FIG. 18, however, counting is performed commonly using an up/down counter irrespective of operation mode while switching processing mode of the up/down counter. Thus, although compact design of the circuit is allowed, for example, when the counter counts up to a predetermined value ad then starts counting down from the value, the continuity of count value is not maintained in at the time of switching of count mode. Thus, the counter is not suitable for performing counting continuously while switching count mode (hereinafter referred to as a first problem). This will be described below.

FIG. 19 is a timing chart for explaining the operation of the counter circuit 900 shown in FIG. 18.

In this example, a 4-bit asynchronous counter switches between the non-inverting output Q and the inverting output NQ according to the control signal SW, so that up-counting is first performed and then down-counting is performed. When switching from up-counting to down-counting occurs, however, the count value changes from 6 to 10. Thus, it is not possible to perform up-counting and down-counting while maintaining the count value before and after switching of count mode using a pulse train having a high frequency.

A scheme for overcoming this problem is proposed, for example, in Japanese Unexamined Patent Application Publication No. 6-216762 (hereinafter referred to as a second patent document). According to the second patent document, a device for inverting the status of each flip-flop and a device for initializing all the flip-flops on each even-numbered pulse train are provided.

The method of counting described in the second patent document will be described below. It is assumed that an asynchronous counter is capable of counting up to a maximum number n, a first pulse train includes i pulses, and a second pulse train includes j pulses.

The counter is reset in advance, and counts from 0 to i for the first pulse train. Then, when the status of the flip-flops of the counter is inverted, the n's complement of the value i is obtained, so that the value of the counter becomes n−i.

The counter then counts from n−i to n−i+j. The difference of interest i−j is the n's complement of n−i+j, which is obtained by inverting the status of the flip-flops again. Thus, an asynchronous counter for performing up-counting and down-counting using a continuous pulse train having a high frequency is implemented.

According to the scheme described in the second patent document, however, since up-counting and down-counting are performed by calculation involving complement values, which is not direct (hereinafter referred to as a second problem).

Furthermore, the schemes of AD conversion described in the first to fifth non-patent documents and the first patent document have drawbacks relating to circuitry scale, circuit area, power consumption, the number of wires for interfacing with other functional units, noise associated with the wires, or consumption current. This will be described below.

Construction of Solid-State Imaging Device According to the Related Art

FIG. 21 is a schematic construction diagram of a CMOS solid-state imaging device (CMOS image sensor) according to the related art, in which an AD converter and a pixel unit are mounted on the same semiconductor substrate. As shown in FIG. 21, a solid-state imaging device 1 includes a pixel unit (imaging unit) 10 in which a plurality of unit pixels 3 is arranged in rows and columns, a driving controller 7 provided externally to the pixel unit 10, a counter (CNT) 24, a column processor 26 including column AD circuits 25 provided for the respective columns, a reference-signal generator 27 including a digital-to-analog converter (DAC) for supplying a reference voltage for AD conversion to the column AD circuits 25 in the column processor 26, and an output circuit 28 including a subtractor circuit 29.

The driving controller 7 includes a horizontal scanning circuit (column scanning circuit) 12 that controls column address or column scanning, a vertical scanning circuit (row scanning circuit) 14 that controls row address or row scanning, and a timing controller 21 that receives a master clock CLK0 via a terminal 5a and that generates various internal clocks to control the horizontal scanning circuit 12, the vertical scanning circuit 14, and the like.

The unit pixels 3 are connected to row control lines 15 that are controlled by the vertical scanning circuit 14 and to vertical signal lines 19 that transfer pixel signals to the column processor 26.

Each of the column AD circuits 25 includes a voltage comparator 252 and a data storage unit (latch) 255, and it has a function of an n-bit AD converter. The voltage comparator 252 compares a reference signal RAMP generated by the reference-signal generator 27 with an analog signal obtained for each row control line 15 (H0, H1, ...) from the unit pixels 3 via the vertical control lines 19 (V0, V1, ...). The data storage unit 255 is a memory that holds a result of counting a time taken by the voltage comparator 252 to finish comparison by the counter 24. The data storage unit 255 includes n-bit latches 1 and 2 that are storage areas independent of each other.

One input terminal RAMP of the voltage comparator 252 receives input of a stairs-like reference signal RAMP generated by the reference-signal generator 27 commonly with the input terminals RAMP of the other voltage comparators 252. The other input terminals of the voltage comparators 252 are connected to the vertical signal lines of the respectively associated columns so that pixel signals from the pixel unit 10 are individually input. Signals output from the voltage comparators 252 are supplied to the data storage units 255. The reference signal RAMP is digitally generated by performing counting based on a count clock CK0 corresponding to the master clock CLK0 (e.g., clock frequencies of these clocks are equal) supplied from the outside of the solid-state imaging device 1 and converting the count value into an analog signal.

The counter 24 performs counting based on the count clock CK0 that is based on the master clock CLK0 (e.g., clock frequencies of these clocks are the same), and supplies count outputs CK1, CK2, . . . , CKn, together with the count clock CK0, commonly to the column AD circuits 25 of the column processor 26.

That is, by providing lines for the count outputs CK1, CK2, . . . , CKn from the counter 24 to the latches of the data storage units 255 provided for the respective columns, the column AD circuits 25 for the respective columns share the single counter 24.

The outputs of the column AD circuits 25 are connected to horizontal signal lines 18. The horizontal signal lines 18 have signal lines for 2n bits, and are connected to the subtractor circuit 29 of the output circuit 28 via 2n sensing circuits (not shown) associated with the respective output lines.

The timing controller 21 instructs, via a control line 12c, the horizontal scanning circuit 12 to read pixel data. In response to the instruction, the horizontal scanning circuit 12 sequentially transfers pixel data held in the latches 1 and 2 to the subtractor circuit 29 of the output circuit 28 by sequentially shifting a horizontal select signal CH(i). That is, the horizontal scanning circuit 12 performs read scanning in the horizontal (row) direction.

The horizontal scanning circuit 12 generates a horizontal select signal CH(i) for performing read scanning in the horizontal (row) direction based on the master clock CLK0 supplied from the outside of the solid-state imaging device 1, similarly to the count clock CK0.

FIG. 22 is a timing chart for explaining an operation of the solid-state imaging unit 1 according to the related art shown in FIG. 21.

For example, for the first reading operation, the count value of the counter 254 is first reset to an initial value "0". Then, after the first reading operation of reading pixel signals from unit pixels 3 on an arbitrary row Hx to the vertical signal lines 19 (V0, V1, . . . ) becomes stable, a reference signal RAMP generated by the reference-signal generator 27, temporally changing so as to form substantially ramp waveform, is input, which is compared by the voltage comparator 252 with a pixel signal voltage on an arbitrary vertical signal line 19 (with a column number Vx).

At this time, simultaneously with the input of the reference signal RAMP to the one input terminal RAMP of the voltage comparator 252, in order to measure a comparison time of the voltage comparator 252 by the counter 24, in synchronization with the ramp waveform voltage generated by the reference-signal generator 27 (t10), the counter 24 starts down-counting from the initial value "0" as the first counting operation.

The voltage comparator 252 compares the ram reference signal RAMP from the reference-signal generator 27 with a pixel signal voltage Vx input via a vertical signal line 19. When these voltages become equal, the voltage comparator 252 inverts its output from H level to L level (t12).

Substantially at the same time with the inversion of the output of the voltage comparator 252, the data storage unit 255 latches the count outputs CK1, CK2, . . . CKn from the counter 24 in accordance with a comparison period in the latch 1 of the data storage unit 255 in synchronization with the count clock CK0, whereby the first iteration of AD conversion is completed (t12).

When a predetermined down-count period elapses (t14), the timing controller 21 stops supply of control data to the voltage comparator 252 and supply of the count clock CK0 to the counter 254. Thus, the voltage comparator 252 stops generating the ramp reference signal RAMP.

In the first reading operation, reset components ΔV of the unit pixels 3 are read, and the reset components ΔV includes offset noise that varies among the unit pixels 3. Generally, however, the variation in the reset components ΔV is small, and the reset levels are common among all the pixels, so that the output of an arbitrary vertical signal line 19 (Vx) is substantially known.

Thus, when the reset components ΔV are read in the first reading operation, it is possible to shorten the comparison period by adjusting the reference signal RAMP. According to this related art, the reset components ΔV are compared in a count period corresponding to 7 bits (128 clock cycles).

In the second reading operation, in addition to the reset components ΔV, signal components Vsig corresponding to the amounts of light incident on the respective unit pixels 3 are read, and the operation similar to the first operation is performed.

More specifically, for the second reading operation, the count value of the counter 254 is first reset to the initial value "0". Then, when the second reading operation of reading pixel signals from the unit pixels 3 on an arbitrary row Hx to the vertical signal lines 19 (V0, V1, . . . ) becomes stable, a reference signal RAMP generated by the reference-signal generator 27 so as to temporally change in a stairs-like manner and have substantially ramp waveform is input, and the voltage comparator 252 compares the reference signal RAMP with a pixel signal voltage on an arbitrary vertical signal line 19 (with a column number Vx).

At this time, simultaneously with the input of the reference signal RAMP to the one input terminal RAMP of the voltage comparator 252, in order to measure a comparison time of the voltage comparator 252 using the counter 24, in synchronization with the ramp waveform voltage generated by the reference-signal generator 27 (t20), the counter 24 starts down-counting from the initial value "0" as the second counting operation.

The voltage comparator 252 compares the ramp reference signal RAMP from the reference-signal generator 27 with a pixel signal voltage Vx input via a vertical signal line 19. When these voltages become equal, the voltage comparator 252 inverts its output from H level to L level (t22).

Substantially at the same time as the inversion of the output of the voltage comparator 252, the data storage unit 255 latches the count outputs CK1, CK2, . . . , CKn from the counter 24 in accordance with the comparison period in synchronization with the count clock CK0, whereby the second iteration of AD conversion is completed (t22).

At this time, the data storage unit 255 holds the count value in the first counting operation and the count value in the second counting operation in different places thereof, namely, in the latch 2. In the second reading operation, combinations of the reset components ΔV and the signal components Vsig of the unit pixels 3 are read.

When a predetermined down-count period elapses (t24), the timing controller 21 stops supply of control data to the voltage controller 252 and supply of the count clock CK0 to the counter 254. Thus, the voltage comparator 252 stops generating the ramp reference signal RAMP.

At specific timing (t28) after the second counting operation is completed, the timing controller 21 instructs the horizontal scanning circuit 12 to read pixel data. In response to the instruction, the horizontal scanning circuit 12 sequentially shifts the horizontal select signal CH(i) supplied to the data storage unit 255 via the control line 12c.

Thus, the count value latched in the data storage unit, i.e., pixel data in the first iteration and the second iteration each represented by n-bit digital data is sequentially output to the outside of the column processor 26 via n (2n in total) horizontal signal lines 18 and is input to the subtractor circuit 29 of the output circuit 28.

The n-bit subtractor circuit 29, for each pixel position, subtracts the pixel data of the first iteration, representing the reset component ΔV of a unit pixel 3, from the pixel data of the second iteration, representing the combination of the reset component ΔV and the signal component Vsig of the unit pixel 3, calculating the signal component Vsig of the unit pixel 3.

Then, similar operation is sequentially performed on a row-by-row basis, whereby image signals representing a two-dimensional image are obtained in the output circuit 28.

However, in the arrangement shown in FIG. 21, the column AD circuits of the respective columns shares the single counter 24, and the results of the first and second counting operations must be held in the data storage unit 255 that functions as a memory. Thus, two n-bit latches are needed for an n-bit signal (2n latches are needed for each bit), causing an increase in circuit area (hereinafter referred to as a third problem).

Furthermore, lines for inputting the count clock CK0 and n count outputs CK1, CK2, . . . , CKn from the counter 24 to the data storage unit 255 are needed. This could increase noise or power consumption (hereinafter referred to as a fourth problem).

Furthermore, in order to hold count values of the first and second counting operations at different locations of the data storage unit 255, 2n signal lines for transmitting the results of the first and second counting operations are needed, which causes an increase in the amount of current (hereinafter referred to as a fifth problem).

Furthermore, before a signal is output to the outside of the device, in order to subtract the count value of the first counting operation from the count value of the second counting operation, 2n signal lines for leading the count values to the n-bit subtractor circuit 29 of the output circuit 28 are needed. This could increase noise or power consumption for transferring data (hereinafter referred to as a sixth problem).

That is, a memory for holding the result of the first reading operation and a memory for holding the result of the second reading operation must be individually provided (i.e., two memories are needed) separately from the counter. Furthermore, signal lines for transmitting n-bit count values from the memories to the counter are needed. Furthermore, in order to transfer the n-bit count values of the first and second counting operations to the subtractor, signal for 2n bits (double) are needed. This increases circuitry scale and circuit area, and also increases noise, consumption current, or power consumption.

Furthermore, when AD conversion and reading operation are executed in parallel, i.e., by a pipeline operation, a memory for holding data obtained by AD conversion is needed separately from a memory for holding the result of counting. Similarly to the third problem, two memories are needed for this purpose, causing an increase in circuit area (hereinafter referred to as a seventh problem).

As a measure for overcoming the third problem, in a proposed column AD converter circuit, a correlated double sampling (CDS) function and an AD conversion function are implemented by providing in series a counter that is commonly used among columns, and a CDS processing unit and a latch for holding the count value of the counter, provided for each column. This is described, for example, in the second non-patent document.

Furthermore, in a proposed scheme for overcoming the second problem, for example, an AD conversion function is implemented by providing a counter for each column in the column processor 26. This is described, for example, in the third and fourth non-patent documents.

In a column AD circuit described in the second non-patent document, AD converters including counters and latches, which perform parallel processing for the vertical signal lines (columns), converts analog signals into digital signals by taking the difference between a reset component and a signal component while suppressing fixed pattern noise of pixels. Thus, subtraction is not needed, and a single counting operation suffices. Furthermore, memories for holding data obtained by AD conversion can be implemented by latches. This serves to avoid increase in circuit area. That is, the third, fifth, sixth, and seventh problems are overcome.

However, lines for inputting the count clock CK0 and n count outputs from the counters to the latches are needed, so that the fourth problem is not overcome.

According to techniques described in the third and fourth non-patent documents, currents from a plurality of pixels that detect light are simultaneously output onto an output bus, and addition and subtraction are performed in terms of currents on the output bus. Then, signals are converted into pulse-width signals having magnitudes in the temporal direction, and the clock cycles of the pulse widths of the pulse-width signals are counted by counter circuits provided for the respective columns, thereby performing AD conversion. Accordingly, wires for count outputs are not needed, i.e., the fourth problem is overcome.

However, handing of a reset component and a signal component is not described, so that the third, fifth, sixth, and seventh problems are not necessarily overcome. Handling of a reset component and a signal component is not described either in the first and fifth non-patent documents.

On the other hand, the first patent document describes handling of a reset component and a signal component. In order to extract voltage data of a pure image from a reset component and a signal component, for example, by correlated double sampling, digital data of the reset component is subtracted from digital data of the signal component for each column, so that the sixth problem is avoided.

However, according to techniques described in the first patent document, counting is performed in an external system interface to generate a count signal, and a count value at a time when a voltage of the reset component or the signal component matches a reference voltage for comparison is saved in a pair of buffers provided for each column. Thus, the scheme of AD conversion is the same as that in the first non-patent document in that a single counter is commonly used by the columns. Thus, the third to fifth and seventh problems cannot be avoided.

SUMMARY OF THE INVENTION

The present invention has been made in view of the situation described above, and it is an object thereof to provide a scheme that overcomes the first and second problems. More preferably, it is an object of the present invention to provide a scheme that overcomes at least one of the third to seventh problems.

According to an aspect of the present invention, an asynchronous counter circuit that is allowed to selectively perform counting in an up-count mode or counting in a down-count mode is provided. The counter circuit includes an initial-value setting processor that sets a count value immediately before switching of count mode as an initial value at a time of the switching of the count mode before starting counting after the count mode is switched.

According to another aspect of the present invention, an analog-to-digital conversion method for converting a difference signal component into digital data, the difference signal component representing a difference between a reference component and a signal component included in an analog signal subject to processing, is provided. A signal corresponding to the reference component and a signal corresponding to the signal component are compared with a reference signal for conversion into digital data, and concurrently with the comparison, counting is performed in a down-count mode or an up-count mode, holding a count value at a time of completion of the comparison. At this time, the counting mode is switched according to whether comparison is being performed for the reference component or the signal component.

According to another aspect of the present invention, an analog-to-digital converter that is suitable for carrying out the AD conversion method described above is provided. The AD converter includes a comparator that compares a signal corresponding to the reference component and a signal corresponding to the signal component with a reference signal for conversion into digital data; and an asynchronous counter that performs counting in a down-count mode or an up-count mode, concurrently with the comparison in the comparator, the counter holding a count value at a time of completion of the comparison in the comparator.

According to the AD conversion method, AD converter, semiconductor device, and electronic apparatus according to the aspects of the present invention, a signal subject to processing, including a reference component and a signal component, is compared with a reference signal for AD conversion, and concurrently with the comparison, counting is performed in a down-count mode or an up-count mode using an asynchronous counter, holding a count value at a time of completion of the comparison. At this time, the counting mode is switched according to whether comparison is being performed for the reference component or the signal component.

BRIEF DESCRIPTION OF THE DRAWINGS

FIG. 4 is a timing chart for explaining an operation of the counter circuit according to the first embodiment shown in FIG. 2;

FIG. 14 is a timing chart for explaining an operation of a column AD circuit of the solid-state imaging device according to the first embodiment shown in FIG. 11;

DESCRIPTION OF THE PREFERRED EMBODIMENTS

Now, embodiments of the present invention will be described in detail with reference to the drawings. The description will first be directed to asynchronous counter circuits according to embodiments of the present invention, and then to examples of application of the asynchronous counter circuits to electronic apparatuses and semiconductor devices.

First Embodiment of the Configuration of Counter Circuit

Figure 1:
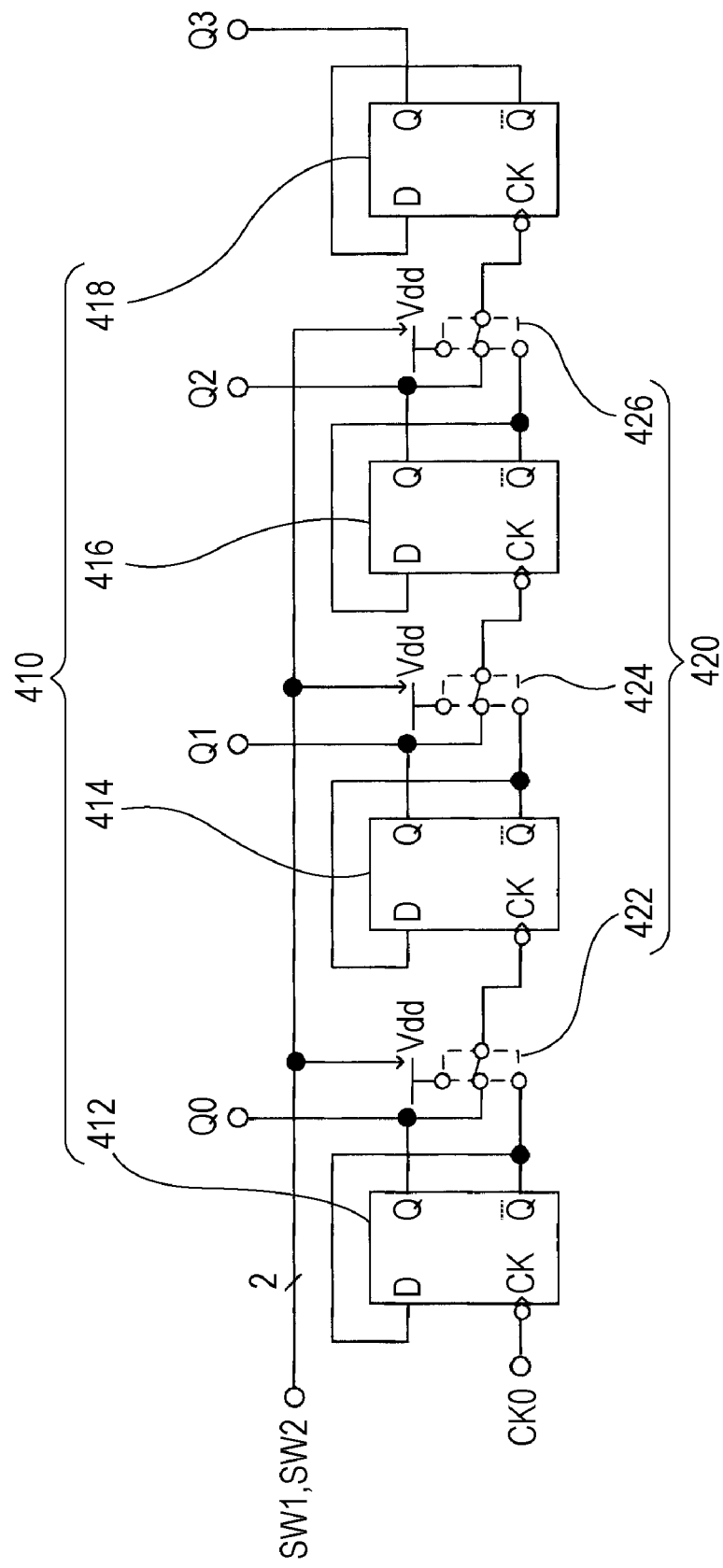
FIG. 1 is a block circuit diagram showing the basic configuration of a first embodiment of an asynchronous counter according to the present invention.
Figure 2:
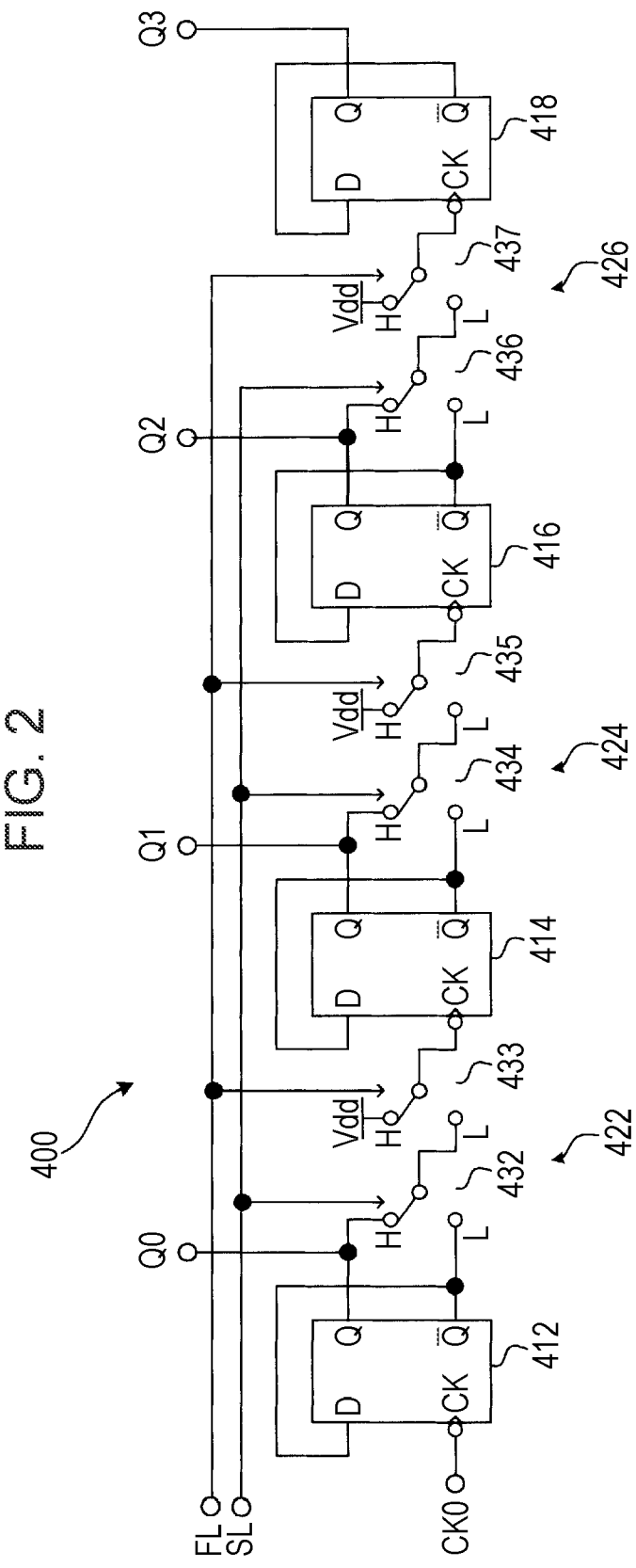
FIG. 2 is a block circuit diagram showing a specific implementation of the basic configuration according to the first embodiment.

FIG. 1 is a block circuit diagram showing the basic configuration of an asynchronous counter according to a first embodiment of the present invention. FIG. 2 is a block circuit diagram showing a specific implementation of the basic configuration according to the first embodiment.

As shown in FIG. 1, a counter circuit 400 according to the first embodiment is implemented by cascade connection of a plurality of negative-edge D flip-flops 412, 414, 416, and 418 (collectively 410). Each of the flip-flops 410 has an inverting output NQ (indicated in FIG. 1 by a horizontal bar over Q) connected to a D input terminal thereof. Thus, the counter circuit 400 is capable of functioning as a 4-bit asynchronous counter. Although four stages (corresponding to four bits) of flip-flops 412, 414, 416, and 418 are shown in FIG. 1, actually, a number of flip-flops corresponding to the number of bits is provided.

Furthermore, between the respective adjacent pairs of the flip-flops 410, the counter circuit 400 includes three-input single-output tri-value switches 422, 424, and 426 (collectively 420) that switch among three values, namely, the non-inverting output Q, the inverting output NQ, and a power supply (Vdd) level. Each of the tri-value switches 420 switches among the three input signals according to 2-bit control signals SW1 and SW2 supplied from a controller (not shown), and inputs a selected signal to a clock terminal of the subsequent flip-flop 410.

Each of the tri-value switches 420 functions as an initial-value setting processor that causes, at a time of switching of count mode, a count value immediately before mode switching to be set as a initial value so that counting is started from the value after the mode switching.

That is, with respect to the cascade connection of a plurality of flip-flops as basic elements of the counter, the tri-value switches 420 are disposed between the respective adjacent pairs of the flip-flops 410. One of the non-inverting output NQ and the inverting output Q of a previous flip-flop 410 is selected as a counter clock and is supplied to the clock terminal CK of a subsequent flip flop 410 so that switching of count mode is allowed, and a count value of the previous flip-flop 410 immediately before mode switching is set to the subsequent flip-flop 410 as an initial value.

More specifically, the tri-value switches 420 can be respectively implemented by a pair of two-input single-output binary switches 432 and 433, a pair of two-input single-output binary switches 434 and 435, and a pair of two-input single-output binary switches 436 and 437, as shown in FIG. 2. These binary switches will be collectively referred to as binary switches 430.

In this example, each of the binary switches 430 is switched according to switching control signals SL and FL generated at different timings as the two-bit switching control signals SW1 and SW2 supplied from a controller (not shown).

The binary switches 432, 434, and 436 at the previous stages switch the non-inverting outputs Q and the inverting outputs NQ of the respectively associated flip-flops 410 according to the switching control signal SL, and pass the results to one of the input terminals of the associated binary switches 433, 435, and 437 at the subsequent stages. The binary switches 433, 435, and 437 at the subsequent stages switches between the data passed from the binary switches 432, 434, and 436 at the previous stages and the power supply level input to the other input terminals thereof according to the switching control signal FL, and input the results to the clock terminals CK of the subsequent flip-flops 410.

For example, the previous binary switch 430 (432, 434, and 436) selects the non-inverting output NQ and the inverting output Q of the preceding flip-flop 430 according to the switching control signal SL, and supplies it to one input terminal of the subsequent binary switch 430 (433, 435, and 437). The switching control signal SL controls the previous binary switch 430 (432, 434, and 436), thereby switching the counting operation of the counter circuit 400 between up-counting and down-counting.

The subsequent binary switch 430 (433, 435, and 437) adjusts the supply of the output (non-inverting output NQ or inverting output Q) of the preceding flip-flop 410, output from the previous binary switch 430 (432, 434, and 436) to the clock terminal of the succeeding flip-flop 410 according to the switching control signal FL.

The switching control signal FL controls the subsequent binary switch 430 (433, 435, and 437) so that the supply of the output of the preceding flip-flop 410 (non-inverting output NQ or inverting output Q) to the clock terminal of the succeeding flip-flop 410 for a predetermined period after switching of count mode, and so that a signal corresponding to a clock is supplied to the clock terminal of the succeeding flip-flop 410 when the supply of non-inverting output NQ or inverting output Q is resumed. Thus, the continuity of count value is maintained when count mode is switched between the up-count mode and the down-count mode. The functions of the switching control signal FL will be described later in detail.

By "maintaining the continuity of count value", although the count value becomes broken when count mode is switched, before starting counting after the mode switching, the final count value in the previous mode is restored so that the counting operation after the mode switching starts from the final count value in the previous mode.

Figure 3A:
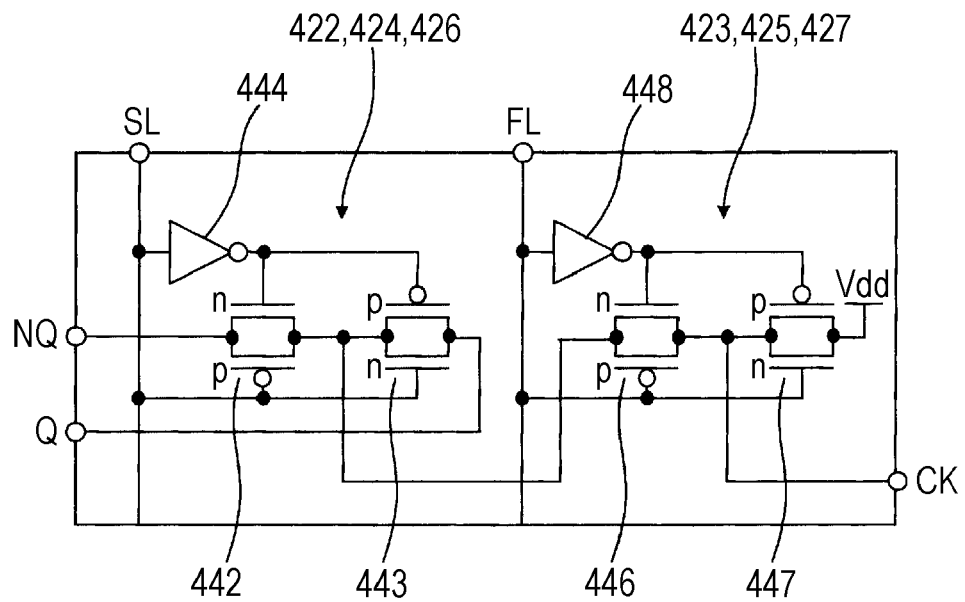
FIGS. 3A and 3B are diagrams showing an example circuit configuration of a binary switch.
Figure 3B:
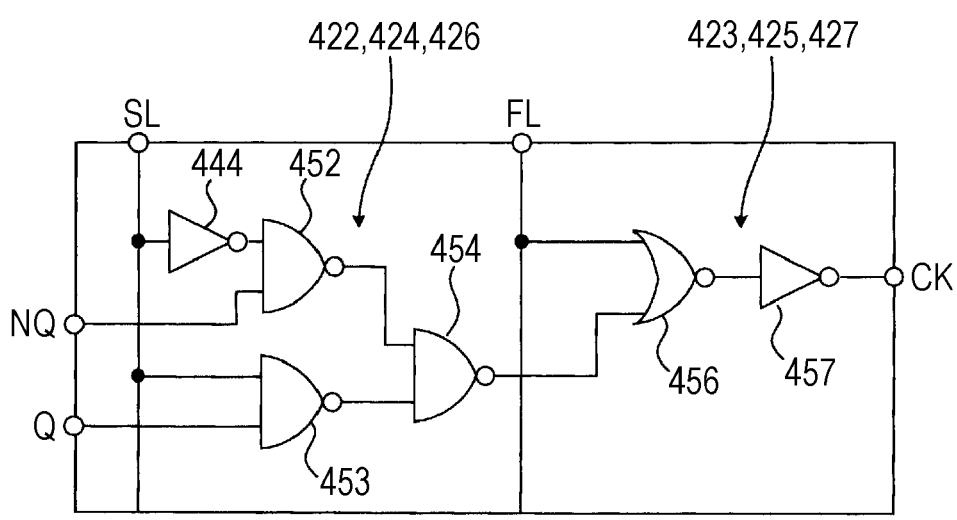

FIGS. 3A and 3B are diagrams showing example circuit configurations of the binary switches 430. FIG. 3A shows an example where each switch is implemented by a transfer gate. All the circuit elements are implemented using CMOS techniques.

In association with the previous binary switches 432, 434, and 436, transfer gates 442 and 443 are provided. In association with the subsequent binary switches 433, 435, and 437, transfer gates 446 and 447 are provided. These transfer gates will be collectively referred to as transfer gates 440.

The input of the transfer gate 442 receives the inverting output NQ of the preceding flip-flop 410. The input of the transfer gate 443 receives the non-inverting output Q of the preceding flip-flop 410. The outputs of the transfer gates 442 and 443 are commonly connected to the input of the transfer gate 446. The input of the transfer gate 447 is connected to a power supply level. The outputs of the transfer gates 446 and 447 are commonly connected to the clock terminal CK of the succeeding flip-flop 410.

Each of the transfer gates 440 is implemented by a CMOS switch including an N-channel transistor n1 and a P-channel transistor p1. The gates (control input terminal) of the transistors n1 and p1 correspond to input terminals of the switching controls signals SL and FL or inverted switching control signals NSL and NFL. The inverted signal NSL is generated by an inverter 444 that inverts the switching control signal SL, and the inverted signal NFL is generated by an inverter 448 that inverts the switching control signal FL.

The CMOS switch including the transistors n1 and p1 selectively outputs the non-inverting output Q or the inverting output NQ of the preceding flip-flop 410 by turning on when the gate of the transistor n1 is High and the gate of the transistor n1 is Low. The CMOS switch may be replaced by an N-channel MOS transistor switch or a P-channel MOS transistor switch including either the transistor n1 or the transistor p1. In that case, however, a problem relating to a threshold voltage Vth occurs. Thus, in this embodiment, the CMOS switch formed by the transistor n1 and p1 is used.

FIG. 3B shows an example where each switch is implemented by a logic gate. In association with the previous binary switches 432, 434, and 436, three two-input NAND gates 452, 453, and 454 are provided. In association with the subsequent binary switches 433, 435, and 437, an OD gate formed by a two-input NOR gate 456 and an inverter 457 is provided.

One input of the NAND gate 452 receives the inverted signal NSL obtained by inverting the switching control signal SL by the inverter 455, and one input of the NAND gate 453 receives the switching control signal SL. The other input of the NAND gate 452 receives the inverting output NQ of the preceding flip-flop 410, and the other input of the NAND gate 453 receives the non-inverting output Q of the preceding flip-flop 410. The outputs of the NAND gates 452 and 453 are connected to the inputs of the NAND gate 454.

One input terminal of the NOR gate 456 receives the output of the NAND gate 454, and the other input terminal thereof receives a switching control signal. The output of the NOR gate 456 is inverted by the inverter 457, and is then led to the clock terminal CK of the succeeding flip-flop 410.

In either FIG. 3A or FIG. 3B, each of the previous binary switches 432, 434, and 436 selectively outputs the non-inverting output Q when the switching control signal SL is at High level, while selectively outputting the inverting output NQ when the switching control signal SL is at Low level.

Each of the subsequent binary switches 433, 435, and 437 selectively outputs the output of the associated previous binary switch 432, 434, or 436 when the switching control signal FL is at Low level, while selectively outputting the power supply level (High level) when the switching control signal FL is at High level.

First Embodiment of the Operation of Counter Circuit

Figure 5A:
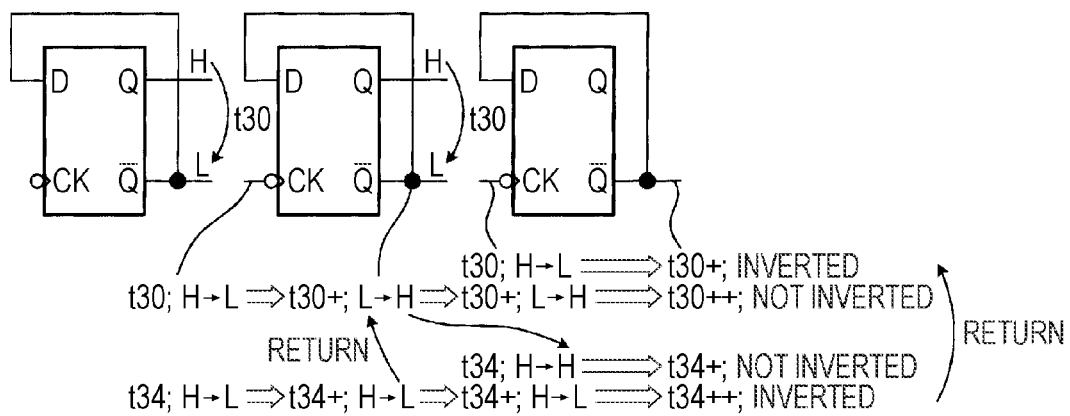
FIGS. 5A and 5B are diagrams showing changes in outputs of flip-flops in the first embodiment.
Figure 5B:
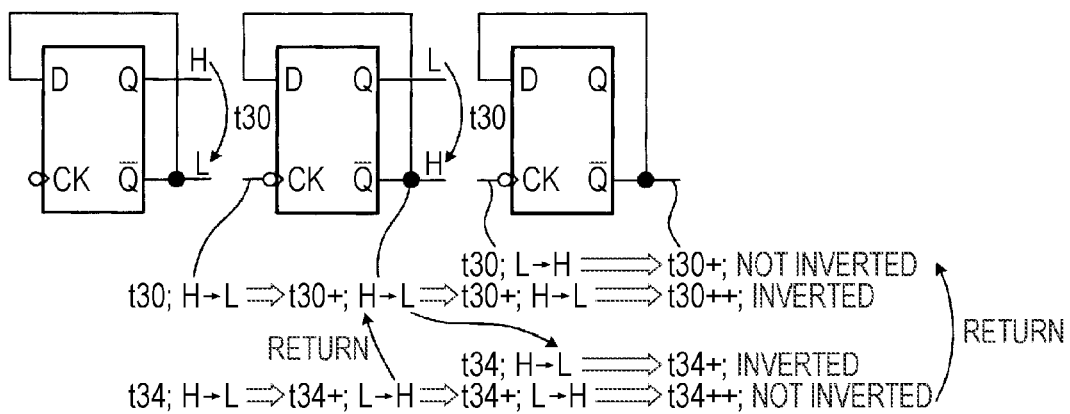

FIG. 4 is a timing chart for explaining the operation of the counter circuit according to the first embodiment shown in FIG. 2. FIGS. 5A and 5B are diagrams for explaining change in the outputs of the flip-flops 410 in the first embodiment.

As described earlier, when the switching control signal SL is at High level and the switching control signal FL is at Low level, each of the previous binary switches 432, 434, and 436 selectively outputs the non-inverting output Q, and each of the subsequent binary switch 433, 435, and 437 selectively outputs the output of the previous binary switch 432, 434, or 436. Thus, between each adjacent pair of the flip-flops 410, the non-inverting output Q of the preceding flip-flop 410 is input to the clock terminal CK of the succeeding flip-flop 410.

In this arrangement, when the clock CK0 is input to the clock terminal CK of the first flip-flop 410, a state transition occurs between the flip-flops 410 for each negative edge of the non-inverting output Q, so that the counter circuit 400 performs an up-counting operation (a period of count values 0 to 6).

After the up-counting operation is performed for a certain period, when the clock CK0 is stopped and the switching control signal SL is inverted from High level to Low level (t30), the counter circuit 400 switches from the up-count mode to the down-count mode, and starts down-counting when the clock CK0 is resumed. In this example, the switching control signal SL is switched from High level to Low level after up-counting is performed from a count value of 0 to a count value of 6.

By the switching of count mode according to the switching control signal at t30, the pair of binary switches 430 selects the inverting output NQ of the preceding flip-flop 410 and inputs it to the clock terminal CK of the succeeding flip-flop 410.

At this time, when the non-inverting output Q of the preceding flip-flop 410 is at High level, i.e., when the inverting output NQ is at Low level, by the switching of the switching control signal SL, a negative edge (transition from H to L) is applied to the clock terminal CK of the succeeding flip-flop 410, so that the output of the succeeding flip-flop 410 is inverted (t30+).

In FIG. 5A, the output of the second flip-flop 410 is inverted from Low level to High level, and the output of the third flip-flop 410 is also inverted (t30+). In FIG. 5B, the output of the second flip-flop 410 is inverted from High level to Low level (t30+).

That is, the count value starts to be broken only at the subsequent stage of a flip-flop 410 in which the non-inverting output Q is at High level, i.e., the inverting output NQ is at Low level, at the time of switching of count mode.

Furthermore, when the output of the succeeding flip-flop 410 is inverted, if the inverting output NQ thereof is inverted from Low level to High level, the clock terminal CK of the further succeeding flip-flop 410 is pulled to High level, so that the output is not inverted (t30++, the third stage in FIG. 5A).

On the other hand, when the inverting output NQ is inverted from High level to Low level, a negative edge is applied to the clock terminal CK of the further succeeding flip-flop 410, so that the output of the succeeding flip-flop 410 is inverted (t30++, the third state in FIG. 5B).

Similarly, the effect of inverting data (from H to L) of the inverting output NQ is propagated up to a flip-flop 410 in which the inverting output NQ is inverted from Low level to High level. In this example, the count value changes from "6" to "10" as shown in FIG. 4.

That is, without taking any measure, when switching from up-counting to down-counting occurs, the count value becomes broken and the continuity of count value is not maintained, so that it is not possible to perform up-counting and down-counting while maintaining the count value before and after the switching.

Thus, in this embodiment, after the switching of the switching control signal SL for switching count mode, before a negative edge of the clock CK0 for down-counting is input to the first flip-flop 410, an active-H one-shot pulse is applied to the subsequent binary switches 433, 435, and 437 as the switching control signal FL (t32 to t34).

Thus, the power supply level (High level) is input to the clock terminals CK of all the negative-edge flip-flops 410. However, the outputs of the negative edge flip-flops 410 do not change before and after the input of the one-shot pulse of the switching control signal FL.

Then, when the one-shot pulse period elapses (t34), the inverting output NQ of the preceding flip-flop 410 is again input to the clock terminal CK. At this time, when the inverting output NQ of the preceding flip-flop 410 is at Low level, a negative edge is applied to the clock terminal CK of the succeeding flip-flop 410, so that the output of the succeeding flip-flop 410 is inverted.

In FIG. 5A, the output of the second flip-flop 410 is inverted from High level to Low level (t34+). In FIG. 5B, the output of the second flip-flop 410 is inverted from Low level to High level, and the output of the third flip-flop 410 is also inverted (t34+).

Furthermore, when the output of the flip-flop 410 is inverted, if the inverting output NQ is inverted from Low level to High level, the clock terminal CK of the succeeding flip-flop 410 is pulled to High level, so that the output is not inverted (t34++, third stage in FIG. 5B).

On the other hand, when the inverting output NQ is inverted from High level to Low level, a negative edge is applied to the clock terminal CK of the further succeeding flip-flop 410, so that the output of the succeeding flip-flop 410 is inverted (t34++, third stage in FIG. 5A). Similarly, the effect of inversion (from H to L) of the inverting output NQ is propagated to a flip-flop 410 in which the inverting output NQ is inverted from Low level to High level.

Thus, in each flip-flop 410 in which the output is inverted in response to switching of count mode according to the switching control signal SL, the output is inverted again, so that the count value is restored.

When the clock CK0 is input again after the operation described above, a state transition occurs between the flip-flops 410 for each negative edge of the inverting output NQ, i.e., for each positive edge of the non-inverting output Q, so that the counter circuit 400 performs a down-counting operation (a period of count values of 6 to 1).

As described above, with the counter circuit 400 according to the first embodiment, the count value changed at the time of switching from up-counting to down-counting is restored to the state after the mode switching after once forcibly pulling the clock terminals of flip-flops 410 to High level by applying an active-H one-shot pulse as the switching control signal FL. If the inverting output NQ of the preceding flip-flop 410 is at Low level when the state after the mode switching is restored, the output of the succeeding flip-flop 410 is inverted, whereby the original count value is restored.

Thus, essentially, the count value before the switching of count mode is maintained. Thus, it is possible to perform down-counting after up-counting while maintaining the continuity of count value.

Down-counting is performed in the negative direction as compared with up-counting. Thus, by performing up-counting by i and then performing down-counting by j, the result of subtraction i−j can be obtained as a result of counting by the counter circuit 400. Advantageously, the count value obtained by switching mode between up-counting and down-counting does not involve complement values, and the result of subtraction can be obtained directly.

With the asynchronous counter circuit 400, it is possible to continuously perform up-counting and down-counting directly by an asynchronous counter, which has hitherto been difficult, by adding simple switches. Since the value before switching is maintained at the time of switching between up-counting and down-counting, it is possible to continuously perform up-counting and down-counting or down-counting and up-counting and to obtain a result of subtraction between a count value of up-counting and a count value of down-counting.

The first embodiment has been described in the context of an example where switching from up-counting to down-counting occurs. The continuity of count value cannot be maintained either when switching from down-counting to up-counting if the count mode is simply switched. By once pulling the clock terminals of flip-flops 410 forcibly to High level using the switching control signal FL before restoring the original count value after the mode switching as described above, essentially, it is possible to maintain the count value before the switching of count mode, it is possible to continuously perform up-counting after down-counting while maintaining the continuity of count value.

Furthermore, even when up-counting and down-counting are performed arbitrarily in combination, it is possible to exercise control so that the original count value is restored at the time of mode switching.

Although an overflow of counting is not detected in the first embodiment, a measure against overflow can be readily implemented using known techniques, for example, by adding an additional bit for overflow or by using a bit for carry or borrow.

Second Embodiment of the Configuration of Counter Circuit

Figure 6:
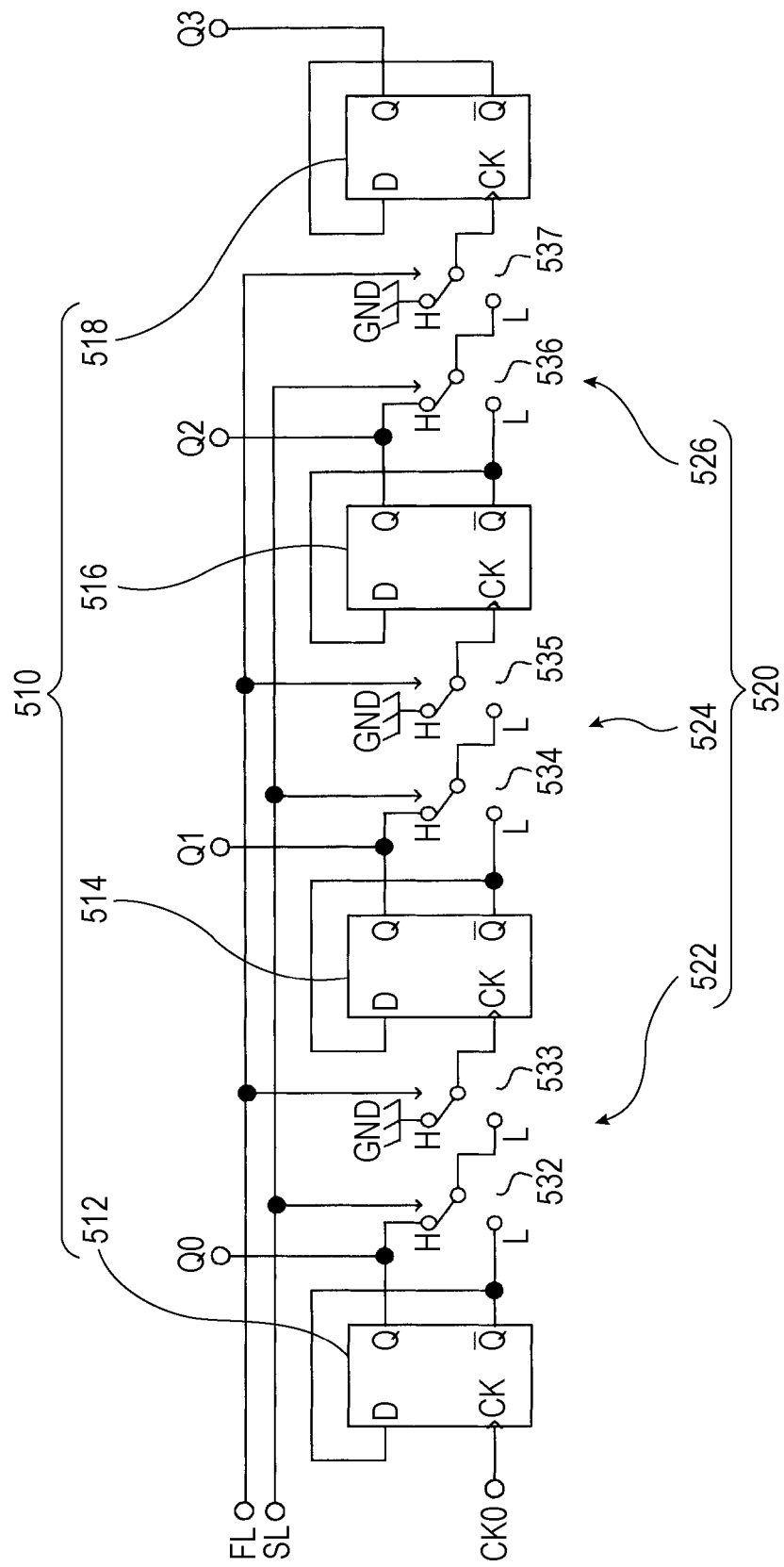
FIG. 6 is a block circuit diagram showing the configuration of a second embodiment of an asynchronous counter according to the present invention.

FIG. 6 is a block circuit diagram showing the configuration of a second embodiment of an asynchronous counter according to the present invention, corresponding to the specific block circuit diagram of the first embodiment shown in FIG. 2.

In the second embodiment, similarly to the first embodiment, three-input single-output tri-value switches 522, 524, and 526 (collectively 520) that each switch among three input signals according to two-bit control signals SW1 and SW2 from a controller (not shown) and input a selected signal to the clock terminal CK of the succeeding flip-flop 510 are provided respectively between the adjacent pairs of flip-flops 510.

Each of the three-input single-output tri-value switches 520 functions as an initial-value setting processor that sets a count value immediately before the mode switching as an initial value so that counting after the mode switching is started from the initial value.

Each of the flip-flop 510 operates based on positive edges instead of negative edges, and in order to deal with the inversion of edge operations, each of the tri-value switches 520 provided between the flip-flops 510 switches among three values, namely, the non-inverting output Q and the inverting output NQ of the associated flip-flop 510 and a ground (GND) level.

More specifically, as shown in FIG. 6, in a counter circuit 500 according to the second embodiment, the three-input single-output tri-value switches 520 respectively include a pair of two-input single-output binary switches 532 and 533, a pair of two-input single-output binary switches 534 and 535, and a pair of two-input single-output binary switches 536 and 537. These binary switches will be collectively referred to as binary switches 530.

Each of the previous binary switches 532, 534, and 536, similarly to the previous binary switches 432, 434, and 436 in the first embodiment, switches between the non-inverting output Q and the inverting output NQ of the associated flip-flop 510 according to the switching control signal SL, and passes the result to one input terminal of the associated subsequent binary switch 533, 535, or 537.

Each of the subsequent binary switches 533, 535, and 537 switches between the data passed from the previous binary switch 532, 534, or 536 and the ground level input to the other input terminal according to the switching control signal FL, and inputs the result to the clock terminal CK of the succeeding flip-flop 510. That is, the second embodiment differs from the first embodiment in that one of the inputs of the subsequent binary switch in the tri-value switch 520 is changed from the power supply level to the ground level.

Each of the previous binary switches 532, 534, and 536 selectively outputs the non-inverting output Q when the switching control signal SL is at High level, while selectively outputting the inverting output NQ when the switching control signal SL is at Low level. Each of the subsequent binary switches 533, 535, and 537 selectively outputs the output of the associated previous binary switch 532, 534, or 536 when the switching control signal FL is at Low level, while outputting the ground level (Low level) when the switching control signal FL is at High level.

Second Embodiment of the Operation of Counter Circuit

Figure 7:
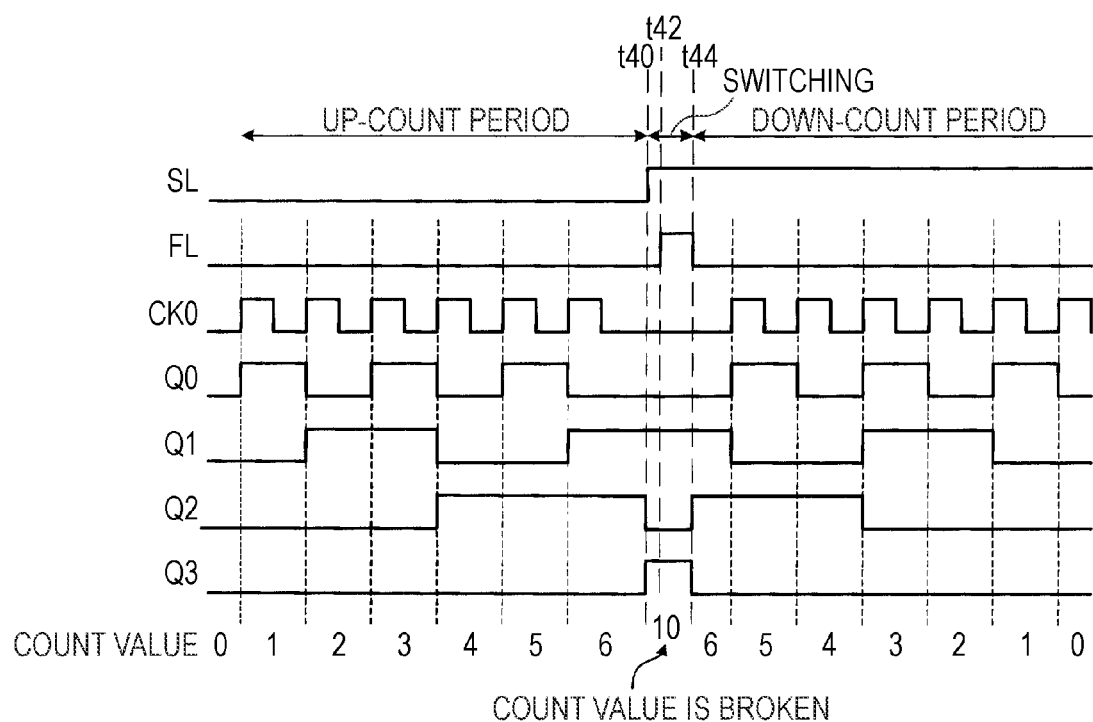
FIG. 7 a timing chart for explaining an operation of the counter circuit according to the second embodiment shown in FIG. 6.
Figure 8A:
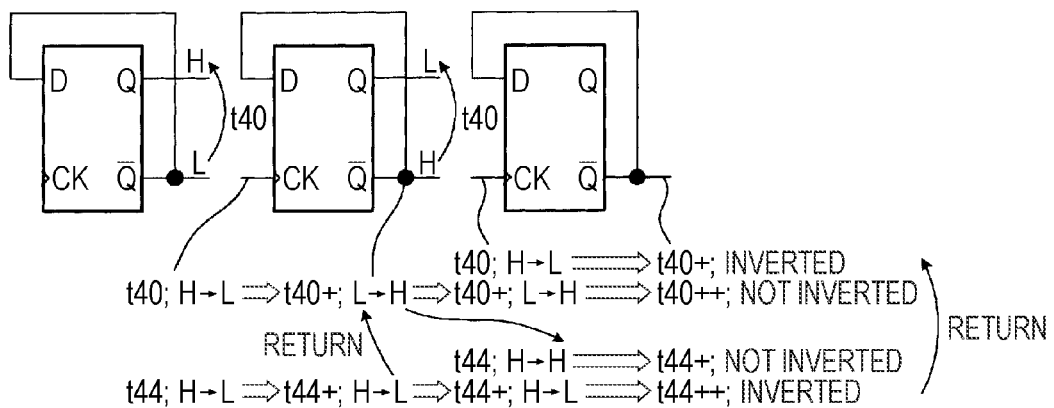
FIGS. 8A and 8B are diagrams showing changes in outputs of flip-flops in the second embodiment.
Figure 8B:
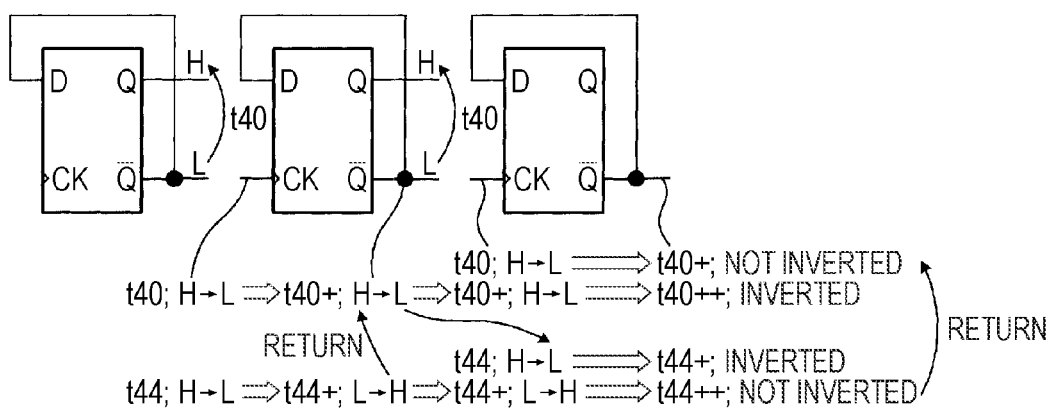

FIG. 7 is a timing chart for explaining the operation of the counter circuit 500 according to the second embodiment shown in FIG. 6. FIGS. 8A and 8B are diagrams for explaining change in the outputs of the flip-flops 510 in the second embodiment.

As opposed to the first embodiment in which up-counting or down-counting is based on negative edges, the second embodiment is modified so that up-counting or down-counting is based on positive edges. The basic ideas are the same as in the first embodiment, and the advantages achieved are also the same.

For example, when the switching control signal SL is at Low level and the switching control signal FL is at Low level, each of the previous binary switches 532, 534, and 536 selectively outputs the inverting output NQ, and each of the subsequent binary switches 533, 535, and 537 selectively outputs the output of the previous binary switch 532, 534, or 536. Thus, between each adjacent pair of flip-flops 510, the inverting output NQ of the preceding flip-flop 510 is input to the clock terminal CK of the succeeding flip-flop 510.

In this arrangement, when the clock CK0 is input to the clock terminal CK of the first flip-flop 510, a state transition occurs between flip-flops 510 for each negative edge of the non-inverting output Q, i.e., for each positive edge of the inverting output NQ, so that the counter circuit 500 performs an up-counting operation (a period of count values of 0 to 6).

After the up-counting operation is performed for a certain period, when the clock CK0 is stopped and the switching control signal SL is inverted from Low level to High level (t40), the counter circuit 500 switches from the up-count mode to the down-count mode, and starts down-counting when the clock CK0 is resumed. In this example, the switching control signal SL is switched from Low level to High level after up-counting is performed from a count value of 0 to a count value of 6.

By the switching of count mode according to the switching control signal SL at t40, the pair of binary switches 530 selects the non-inverting output Q of the preceding flip-flop 510 and inputs it to the clock terminal CK of the succeeding flip-flop 510.

At this time, when the inverting output NQ of the preceding flip-flop 510 is at High level, by the switching of the switching control signal SL, a positive edge (from L to H) is applied to the clock terminal CK of the succeeding flip-flop 510, so that the output of the succeeding flip-flop 510 is inverted (t40+).

In FIG. 8A, the output of the second flip-flop 510 is inverted from Low level to High level, and the output of the third flip-flop 510 is also inverted (t30+). In FIG. 8B, the output of the second flip-flop 510 is inverted from High level to Low level (t30+).

That is, the count value starts to be broken only at the subsequent stage of a flip-flop 510 in which the inverting output NQ is at Low level, i.e., the non-inverting output Q is at High level, at the time of the switching of count mode.

When the output of the succeeding flip-flop 510 is inverted, if the non-inverting output Q thereof is inverted from High level to Low level, the clock terminal CK of the further succeeding flip-flop 510 is pulsed to Low level, so that the output thereof is not inverted (t40++, third stage in FIG. 8A).

On the other hand, when the non-inverting output Q is inverted from Low level to High level, a positive edge is applied to the clock terminal CK of the further succeeding flip-flop 510, so that the output of the flip-flop 510 is inverted (t40++, third stage in FIG. 8B).

Similarly, the effect of inverting data (from L to H) of the non-inverting output Q is propagated to a flip-flop 510 in which the non-inverting output Q is inverted from High level to Low level. In this example the count value changes from "6" to "10", as shown in FIG. 7.

That is, without taking any measure, similarly to the first embodiment, when switching from up-counting to down-counting occurs, the count value becomes broken and the continuity of count value is not maintained. Thus, it is not possible to perform up-counting and down-counting continuously while maintaining the count value before and after the switching.

Thus, in the second embodiment, after the switching control signal SL for switching count mode, before a positive edge of the clock CK0 for down-counting is input to the first flip-flop 510, an active-H one-shot pulse is applied to the subsequent binary switches 533, 535, and 537 as the switching control signal FL (t42 to t44).

Thus, the ground level (Low level) is input to the clock terminals CK of all positive-edge flip-flops 510. However, the outputs of the positive-edge flip-flops 510 do not change before and after the one-shot pulse of the switching control signal FL is input.

Then, when the one-shot pulse period elapses (t44), the non-inverting output Q of the preceding flip-flop 510 is again input to the clock terminal CK. At this time, if the non-inverting output Q of the preceding flip-flop 510 is at High level, a positive edge is applied to the clock terminal CK of the succeeding flip-flop 510, so that the output of the succeeding flip-flop 510 is inverted.

In FIG. 8A, the output of the second flip-flop 510 is inverted from Low level to High level (t44+). In FIG. 8B, the output of the second flip-flop 510 is inverted from High level to Low level, and the output of the third flip-flop 510 is also inverted (t44+).

Furthermore, when the output of the flip-flop 510 is inverted, if the inverting output NQ thereof is inverted from High level to Low level, the clock terminal CK of the succeeding flip-flop 510 is pulled to Low level, so that the output thereof is not inverted (t44++, third stage in FIG. 8B).

On the other hand, when the inverting output NQ is inverted from Low level to High level, a positive edge is applied to the clock terminal CK of the further succeeding flip-flop 510, so that the output of the succeeding flip-flop 510 is inverted (t44++, third stage in FIG. 8A). Similarly, the effect of inverting data (from L to H) of the non-inverting output Q is propagated to a flip-flop 510 in which the non-inverting output Q is inverted from High level to Low level.

Thus, also in the configuration according to the second embodiment, in each flip-flop 510 in which the output is inverted in response to switching of count mode according to the switching control signal SL, the output is inverted again, so that the original count value is restored.

When the clock CK0 is input again after the operation described above, a state transition occurs between the flip-flops 510 for each negative edge of the inverting output NQ, i.e., for each positive edge of the non-inverting output Q, so that the counter circuit 500 performs a down-counting operation (a period of a count value of 6 to a count value of 0).

As described above, with the counter circuit 500 according to the second embodiment, the count value changed at the time of switching from up-counting to down-counting is once pulling the clock terminals of flip-flops 510 forcibly to Low level before restoring the stage after the mode switching by applying an active-H one-shot pulse as the switching control signal FL. If the non-inverting output Q of the preceding flip-flop 510 is at High level when the state after the mode switching is restored, the output of the succeeding flip-flop 510 is inverted, whereby the original count value is restored.

Thus, essentially, the count value before the switching of count mode is maintained. Thus, it is possible to perform down-counting after up-counting while maintaining the continuity of count value.

Down-counting is performed in the negative direction as compared with up-counting. Thus, by performing up-counting by i and then performing down-counting by j, the result of subtraction i−j can be obtained as a result of counting by the counter circuit 400.

The second embodiment has been described in the context of an example where switching from up-counting to down-counting occurs. The continuity of count value cannot be maintained either when switching from down-counting to up-counting if the count mode is simply switched. By once pulling the clock terminals of flip-flops 510 forcibly to Low level using the switching control signal FL before restoring the original count value after the mode switching as described above, essentially, it is possible to maintain the count value before the switching of count mode, it is possible to continuously perform up-counting after down-counting while maintaining the continuity of count value.

Furthermore, even when up-counting and down-counting are performed arbitrarily in combination, it is possible to exercise control so that the original count value is restored at the time of mode switching.

Although an overflow of counting is not detected in the second embodiment, a measure against overflow can be readily implemented using known techniques, for example, by adding an additional bit for overflow or by using a bit for carry or borrow.

Third Embodiment of the Configuration of Counter Circuit

Figure 9:
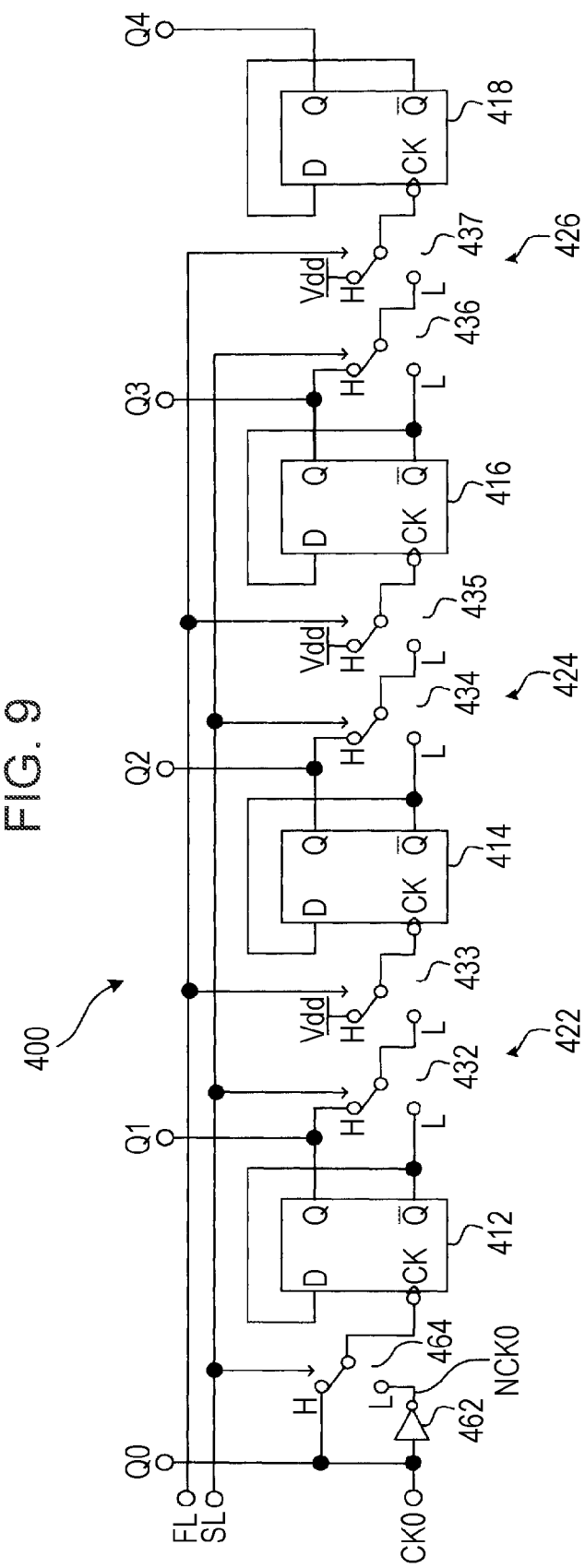
FIG. 9 is a block circuit diagram showing the configuration of a third embodiment of an asynchronous counter according to the present invention.

FIG. 9 is a block circuit diagram showing the configuration of a third embodiment of an asynchronous counter according to the present invention, corresponding to the specific circuit block diagram according to the first embodiment shown in FIG. 2.

In a counter circuit 400 according to the third embodiment, an arrangement for switching the clock signal input to the clock terminal CK of the first flip-flop 412 in the counter circuit 400 according to the first embodiment shown in FIG. 2 is additionally provided. Furthermore, in the counter circuit 400 as a whole, the clock CK0 is used as the least significant bit Q0, and count outputs of the flip-flops 410 as the other bits Qx (Q1 to Q4 in this embodiment) are shifted higher by one bit compared with the first embodiment.

More specifically, the counter circuit 400 in the third embodiment includes an inverter 462 that inverts the clock CK0, and a two-input single output binary switch 464 that selects the clock CK0 or an inverted clock NCK0 inverted by the inverter 462 and inputs it to the clock terminal CK of the first flip-flop 412, i.e., switches whether to invert the clock CK0.

The binary switch 464 selectively outputs the clock CK0 when the switching control signal SL is at High level, while selectively outputting the inverted clock NCK0 when the switching control signal SL is at Low level.

Third Embodiment of the Operation of Counter Circuit

Figure 10:
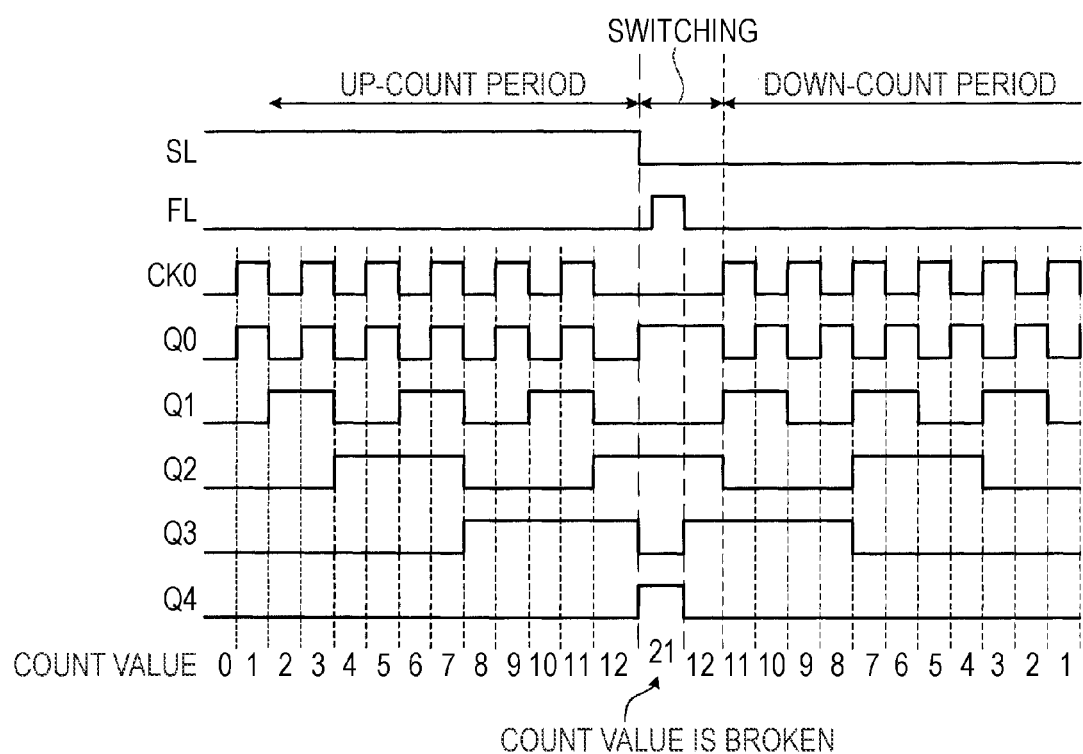
FIG. 10 a timing chart for explaining an operation of the counter circuit according to the third embodiment shown in FIG. 9.

FIG. 10 is a timing chart for explaining the operation of the counter circuit 400 according to the third embodiment shown in FIG. 9.

As opposed to the first embodiment in which up-counting or down-counting is based on negative edges, in the third embodiment, the clock CK0 is used as the least significant bit Q0. Although descriptions corresponding to those relating to FIGS. 5A and 5B will be omitted, the basic ideas are the same as in the first embodiment, and the same advantages are achieved.

Furthermore, by using the clock CK0 as the least significant bit Q0, the number of count bits is increased by one, i.e., doubled, compared with the first embodiment. Furthermore, since High level and Low level of the clock CK0 contribute to count values, counting operations are performed based on both edges of the clock CK0, so that the speed of counting operations is doubled.

Similarly to the application of the second embodiment to the first embodiment, the third embodiment can also be modified by replacing the negative-edge flip-flops 410 with the positive-edge flip-flops 510 so that up-counting or down-counting is performed based on positive edges.

Applications of Asynchronous Counter

Now, examples of application of asynchronous counters according to embodiments of the present invention to electronic apparatuses and semiconductor devices will be described. The following description will be given in the context of examples where a CMOS imaging device, which is an example of X-Y-addressed solid-state imaging device, is used. It is assumed that all the pixels of the CMOS imaging device are implemented by NMOS transistors.

This, however, is only an example, and the applications of the embodiments are not limited to MOS imaging devices. All the embodiments described below can be applied to any semiconductor device for detecting distribution of physical quantity, including a line or a matrix of unit elements that are sensitive to electromagnetic waves input from the outside, such as light or radiation.

First Embodiment of the Construction of Solid-State Imaging Device

Figure 11:
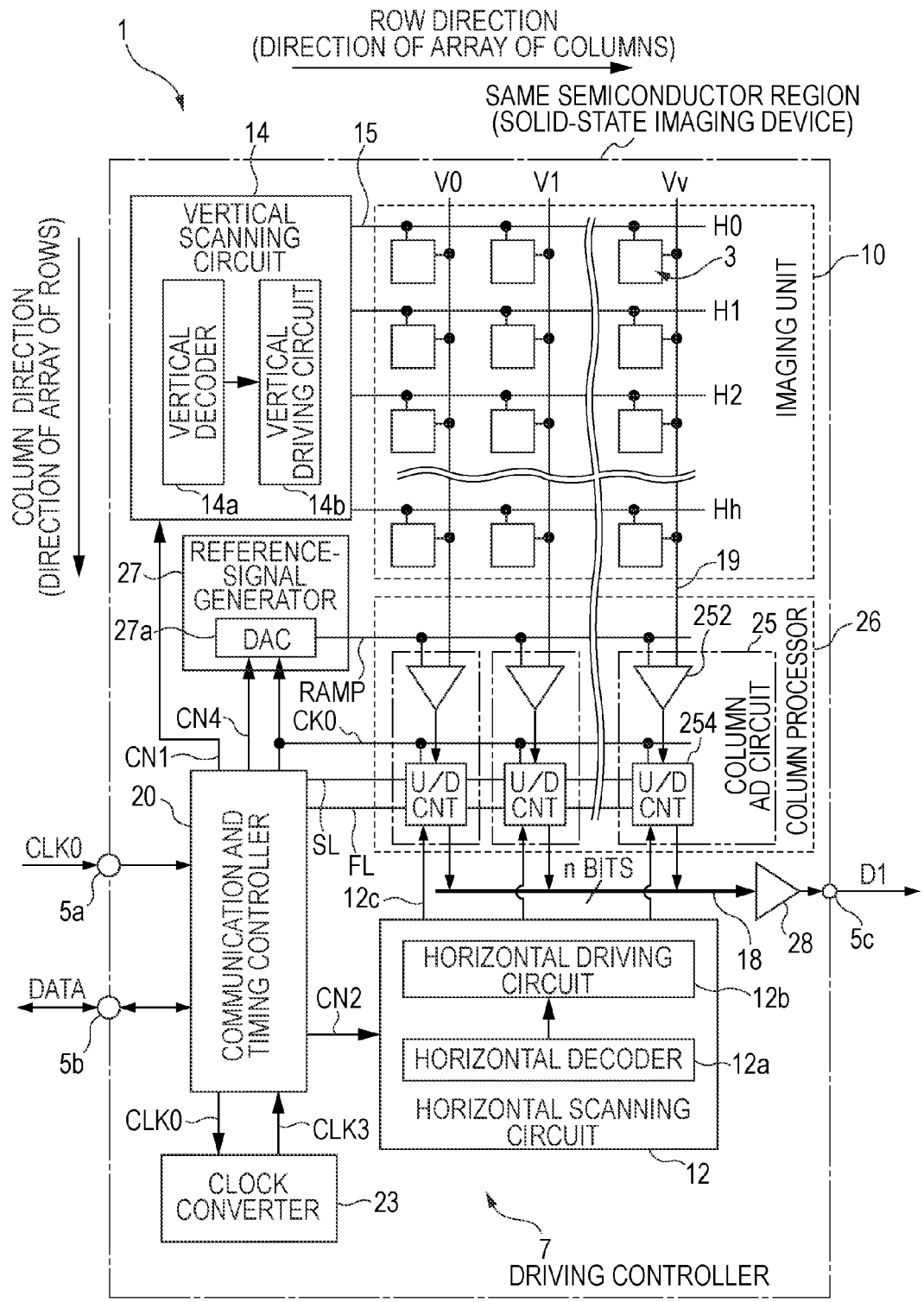
FIG. 11 is a schematic diagram showing the construction of a CMOS solid-state imaging device according to a first embodiment of the present invention.

FIG. 11 is a schematic diagram showing the construction of a CMOS solid-state imaging device (CMOS image sensor), which is a semiconductor device according to a first embodiment of the present invention. The CMOS solid-state imaging device is also an electronic apparatus according to an embodiment of the present invention.

A solid-state imaging device 1 includes a pixel unit in which a plurality of pixels each including a photoreceptor element (which is an example of charge generator) that outputs a voltage signal corresponding to the amount of incident light is arranged in rows and columns (i.e., in a two-dimensional matrix shape). In the solid-state imaging device 1, correlated-double-sampling (CDS) processing units and analog-to-digital converters (ADCs) are provided in association with the respective columns.

By "CDS processing units and ADCs are provided in association with the respective columns", it is meant that a plurality of CDS processing units and ADCs are provided substantially in parallel to vertical signal lines 19 of the columns. The plurality of CDS processing units and ADCs, when viewed in plan, may be both provided on one end of the pixel unit 10 with respect to the column direction (on the output side, i.e., on the lower side as viewed in FIG. 11), or separately provided on one end (on the output side, i.e., on the lower side as viewed in FIG. 11) and on the other end (on the upper side as viewed in FIG. 11) of the pixel unit 10 with respect to the column direction, respectively. In the latter case, preferably, horizontal scanning units that perform horizontal scanning with respect to the horizontal direction are provided separately on both ends so that the horizontal scanning units operate independently of each other.

In a typical example where CDS processing units and ADCs are provided in association with the respective columns, in a region provided on the output side of an imaging unit, referred to as a column region, CDS processing units and ADCs are provided in association with the respective columns, and signals are sequentially read out to the output side. That is, the arrangement is a column-based arrangement. Without limitation to the column-based arrangement, a CDS processing unit and an ADC may be provided in association with each set of (e.g., two) adjacent vertical signal lines 19 (columns), or a CDS processing unit and an ADC may be provided in association with each set of every N-th (N is a positive integer, with (N−1) intervening lines) vertical signal line 19 (column).

According to the above arrangements except for the column-based arrangement, a plurality of vertical signal lines 19 (columns) shares a CDS processing unit and an ADC, so that a switching circuit that supplies pixel signals for a plurality of columns, supplied from the pixel unit 10, to the CDS processing unit and the DAC is provided. Depending on processing that is executed downstream, for example, a memory that holds output signals must be provided.

In any case, by providing a CDS processing unit and an ADC for a plurality of vertical signal lines 19 (columns) so that processing of pixel signals is performed after reading pixel signals on a column-by-column basis, compared with an arrangement in which similar signal processing is performed in individual unit pixels, the construction of each unit pixel is simplified. This allows an image sensor to have an increased number of pixels, to be implemented in a reduced size, and to be manufactured at a lower cost.

Furthermore, it is possible to concurrently process pixel signals of one line by a plurality of signal processors provided in association with the respective columns. This allows the signal processors to operate at a lower speed compared with a case where processing is performed in an output circuit or on the outside of the device by a CDS processing unit and an ADC. This is advantageous in terms of power consumption, bandwidth characteristics, noise, and so forth. In other words, when power consumption and bandwidth characteristics are equalized, high-speed operation of the sensor as a whole is allowed.

In the case of the column-based arrangement, low-speed operation is allowed. This is advantageous in terms of power consumption, bandwidth characteristics, noise, and so forth. Also advantageously, a switching circuit is not needed. The embodiments will be described below in the context of the column-based arrangement unless otherwise specified.

As shown in FIG. 11, the solid-state imaging device 1 according to the first embodiment includes the pixel unit (imaging unit) 10 in which a plurality of unit pixels 3 is arranged in rows and columns, a driving controller 7 provided externally to the pixel unit 10, a column processor 26, a reference-signal generator 27 for supplying a reference voltage for AD conversion to the column processor 26, and an output circuit 28.

As needed, an automatic gain control (AGC) circuit for amplifying signals may be provided upstream or downstream of the column processor 26 in the same semiconductor region where the column processor 26 is provided. When AGC is exercised upstream of the column processor 26, analog amplification is performed. When AGC is exercised downstream of the column processor 26, digital amplification is performed. Since signal levels could be deteriorated when n-bit digital data is simply amplified, preferably, analog amplification is performed before conversion into digital signals.

The driving controller 7 exercises control for sequentially reading signals of the pixel unit 10. For example, the driving controller 7 includes a horizontal scanning circuit (column scanning circuit) 12 that controls column addressing and column scanning, a vertical scanning circuit (row scanning circuit) 14 that controls row addressing and row scanning, and a communication and timing controller 20 that generates an internal clock.

The solid-state imaging device 1 may include a clock converter 23, which is an example of a high-speed-clock generator that generates pulses of a clock having a higher frequency than an input clock, as indicated by a dotted line in the proximity of the communication and timing controller 20. A terminal 5a of the solid-state imaging device 1 receives input of a master clock CLK0. The master clock CLK0 has pulses that serve as a base for various driving pulses for capturing analog pixel signals to be processed from the pixel unit 10 to the column processor 26.

By using signals originating from the high-speed clock generated from the clock converter 23, operation such as AD conversion can be executed quickly. Furthermore, motion extraction or compression that requires high-speed calculation can be executed using the high-speed clock. Furthermore, it is possible to serialize parallel data output from the column processor 26 and to output serial video data D1 to the outside of the device. Thus, the arrangement allows output at a high speed with a number of terminals smaller than the number of bits of data obtained by AD conversion.

The clock converter 23 includes a multiplier circuit 23a that generates pulses having a clock frequency that is faster than an input clock frequency. The clock converter 23 receives a low-speed clock CLK2 from the communication and timing controller 20, and generates therefrom a clock having a frequency that is twice as high or even higher. The multiplier circuit 23a of the clock converter is a k1 multiplier circuit, where k1 denotes a multiplier of the frequency of the low-speed clock CLK2, and can be implemented using various known circuits.

Although some rows and columns are omitted in FIG. 11 for simplicity, actually, several tens to several thousands of unit pixels 3 are arranged on each row and on each column. Each of the unit pixels 3 typically includes a photodiode as a photoreceptor element (charge generator), and an intra-pixel amp having an amplifying semiconductor device (e.g., a transistor).

The intra-pixel amp is implemented, for example, by a floating-diffusion amp. For example, an amp including four transistors in relation to the charge generator, namely, a read-select transistor, which is an example of a charge reader (transferring gate/reading gate), a reset transistor, which is an example of a reset gate, a vertical-select transistor, and a source-follower amplifying transistor, which is an example of a detector that detects change in the potential of floating diffusion, may be used. This arrangement is typical in a CMOS sensor.

Alternatively, as described in Japanese Patent No. 2708455, an arrangement including three transistors may be used, namely, an amplifying transistor for amplifying a signal voltage corresponding to signal charges generated by the charge generator, connected to a drain line (DRN), a reset transistor for resetting the charge generator, and a read-select transistor (transferring gate) that is scanned by a vertical shift register via a transferring line (TRF).

As other components of the driving controller 7, the horizontal scanning circuit 12, the vertical scanning circuit 14, and the communication and timing controller 20 are provided. The horizontal scanning circuit 12 functions as a reading scanner that reads a count value from the column processor 26. The components of the driving controller 7 are formed together with the pixel unit 10 in a semiconductor region of single-crystal silicon or the like using techniques used to manufacture semiconductor integrated circuits, forming a solid-state imaging device, which is an example of a semiconductor system.

The unit pixels 3 are connected to the vertical scanning circuit 14 via row control lines 15 for row selection, and are connected via the vertical signal lines 19 to the column processor 26 in which the column AD circuits 25 are provided for the respective columns. The row control lines 15 generally refer to lines running from the vertical scanning circuit 14 into pixels.

The horizontal scanning circuit 12 and the vertical scanning circuit 14 respectively include decoders, so that shift operations (scanning) are started in response to control signals CN1 and CN2 supplied from the communication and timing controller 20. Thus, the row control lines 15 include lines for transferring various pulse signals for driving the unit pixels 3 (e.g., a reset pulse RST, a transfer pulse TRF, and a DRN control pulse DRN).

Although not shown, the communication and timing controller 20 includes a functional block corresponding to a timing generator (an example of read-address controller) that supplies clocks needed for the operation of the components and pulse signals at specific timings, and a functional block corresponding to a communication interface that receives a master clock CLK0 via a terminal 5a, that receives data DATA instructing an operation mode or the like via a terminal 5b, and that outputs data including information of the solid-state imaging device 1.

For example, the communication and timing controller 20 outputs a horizontal address signal to a horizontal decoder 12a and a vertical address signal to a vertical decoder 14a so that the respective decoders 12a and 14a select corresponding row and column.

Since the unit pixels 3 are arranged in a two-dimensional matrix shape, analog pixel signals that are generated by the pixel-signal generators 5 and output in the column direction via the vertical signal lines are accessed and captured on a row-by-row basis (in a column-parallel manner), i.e., vertical-scan reading is performed. Then, access in the row direction, i.e., the direction of array of the columns, is performed to read pixel signals (digitized pixel data in this embodiment) to the output side, i.e., horizontal-scan reading is performed. This serves to improve the speed of reading pixel signals or pixel data. Obviously, without limitation to scan reading, only information of unit pixels 3 needed may be read by random access, i.e., by directly specifying addresses of unit pixels 3 to be read.

Furthermore, in this embodiment, the communication and timing controller 20 supplies a clock CLK1 having the same frequency as the master clock CLK0 input via the terminal 5a, a clock having a half frequency, or a low-speed clock having a further divided frequency to the components in the device, e.g., the horizontal scanning circuit 12, the vertical scanning circuit 14, or the column processor 26. Hereinafter, the clock having the half frequency, and clocks having even lower frequencies in general, will be referred to as low-speed clocks CLK2.

The vertical scanning circuit 14 selects a row of the pixel unit 10 and supplies pulses needed for the row. For example, the vertical scanning circuit 14 includes the vertical decoder 14a for defining a row to be read in the vertical direction (i.e., for selecting a row of the pixel unit 10), and a vertical driving circuit 14 for driving the row control lines 15 for the unit pixels 3 on a read row address defined by the vertical decoder 14a by supplying pulses thereto. In addition to a row for reading signals, the vertical decoder 14a also selects a row for electronic shutter or the like.

The horizontal scanning circuit 12, in synchronization with the low-speed clocks CLK2, sequentially selects the column AD circuits 25 of the column processor 26, leading signals of the column AD circuits 25 to the horizontal signal lines (horizontal output lines) 18. For example, the horizontal scanning circuit 12 includes the horizontal decoder 12a for defining a column to be read in the horizontal direction (for selecting the individual column AD circuits 25 in the column processor 26), and a horizontal driving circuit 12b for leading signals of the column processor 26 to the horizontal signal lines 18 according to a read address defined by the horizontal decoder 12a. The number of horizontal signal lines 18 corresponds to the number n (n is a positive integer) of bits of signals handled by the column AD circuits 25. For example, if n is ten, ten horizontal signal lines 18 are provided correspondingly to the number n of bits.

In the solid-state imaging device 1 constructed as described above, pixel signals output from the unit pixels 3 are supplied to the column AD circuits 25 of the column processor 26 via the vertical signal lines 19 on a column-by-column basis.

Each of the column AD circuits 25 of the column processor 26 receives signals of pixels of one line and processes the signals. For example, each of the column AD circuits 25 includes an analog-to-digital converter (ADC) that converts analog signals into, for example, 10-bit digital data based on the low-speed clock CLK2.

Although the construction of the ADC will be described later in detail, counting based on clock signals is started when a ramped reference signal (reference voltage) RAMP is supplied to a voltage comparator, and analog pixel signals input via the vertical signal lines 19 are compared with the reference signal RAMP to carry out counting until pulse signals are obtained, whereby AD conversion is performed.

At this time, by suitably configuring the circuit, together with AD conversion, with regard to voltage-mode pixel signals input via the vertical signal lines 19, the difference between a signal level immediately before the pixel is reset (noise level) and a true signal level Vsig in accordance with the amount of light received can be calculated. Thus, it is possible to remove a noise component called fixed pattern noise (FPN) or reset noise.

Pixel data digitized by the column AD circuits 25 is transferred to the horizontal signal lines 18 via a horizontal selecting switch (not shown) that is driven according to horizontal select signals supplied from the horizontal scanning circuit 12, and is then input to the output circuit 28. The number of bits is not limited to 10, and may be less than 10 (e.g., 8) or greater than 10 (e.g., 14).

According to the construction described above, the pixel unit 10 including a matrix of photoreceptor elements that act as charge generators sequentially outputs pixel signals for respective columns on a line-by-line basis. Then, a frame image, i.e., an image corresponding to the matrix of photoreceptors in the pixel unit 10, is presented as a set of pixel signals for the entire pixel unit 10.

Details of Reference-Signal Generator and Column AD Circuits

The reference-signal generator 27 includes a digital-to-analog converter (DAC) 27. The reference-signal generator 27 generates stairs-like ramp waveform based on control data CN4 from the communication and timing controller 20, in synchronization with a count clock CK0, and supplies the ramp waveform as a reference voltage for AD conversion (ADC reference signal) to the individual column AD circuits 25 of the column processor 26. Although not shown, preferably, a filter for removing noise is provided.

By generating the sawtooth-shaped stairs-like wave based on a high-speed clock supplied from the clock converter 23, e.g., a multiplied clock generated by the multiplier circuit, it is possible to cause the wave to changes faster than in a case where the wave is generated based on the master clock CLK0 input via the terminal 5a.

The control data CN4 supplied from the communication and timing controller 20 to the DAC 27a of the reference-signal generator 27 causes the ratio of change in digital data with respect to time to be constant so that the ramp voltage has the same gradient (ratio of change) on each comparing operation. For example, the count value is changed by 1 in each unit time.

Each of the column AD circuits 25 includes a voltage comparator 252 that compares the reference signal RAMP generated by the DAC 27a of the reference-signal generator 27 with analog pixel signals obtained from the unit pixels 3 via the vertical signal lines 19 (V0, V1, ... ) for each of the row control lines 15 (H0, H1, ... ), and a counter 254 that counts time for completion of comparing operations of the voltage comparator 252 and holding the result. Thus, the column AD circuit 25 has a function of n-bit AD conversion.

The communication and timing controller 20 functions as a controller that switches the mode of counting by the counter 254 according to whether a reset component $\Delta V$ or a signal component Vsig of a pixel signal the voltage comparator 252 is executing a comparing operation for. A control signal CN5 for instructing whether the counter 254 is to operate in down-count mode or up-count mode is input from the communication and timing controller 20 to the counter 254 of each of the column AD circuits 25.

In addition to the clock CK0, from the communication and timing controller 20 to the counter 254 of each of the column AD circuits, a switching control signal SL for instructing the counter 254 to operate in a down-count mode or an up-count mode and a switching control signal FL for maintaining the continuity of count value at the time of switching of count mode are input.

One input terminal RAMP of the voltage comparator 252 receives input of the stairs-like reference signal RAMP generated by the reference-signal generator 27, commonly with the input terminals RAMP of the other voltage comparators 252. The other input terminals of the voltage comparators 252 are respectively connected to the vertical signal lines 19 of the associated columns so that pixel signals can be individually input from the pixel unit 10. Signals output from the voltage comparator 252 are supplied to the counters 254.

To a clock terminal CK of the counter 254, a count clock CK0 is input from the communication and timing controller 20, commonly with the clock terminals CK of the other counters 254.

Figure 21:
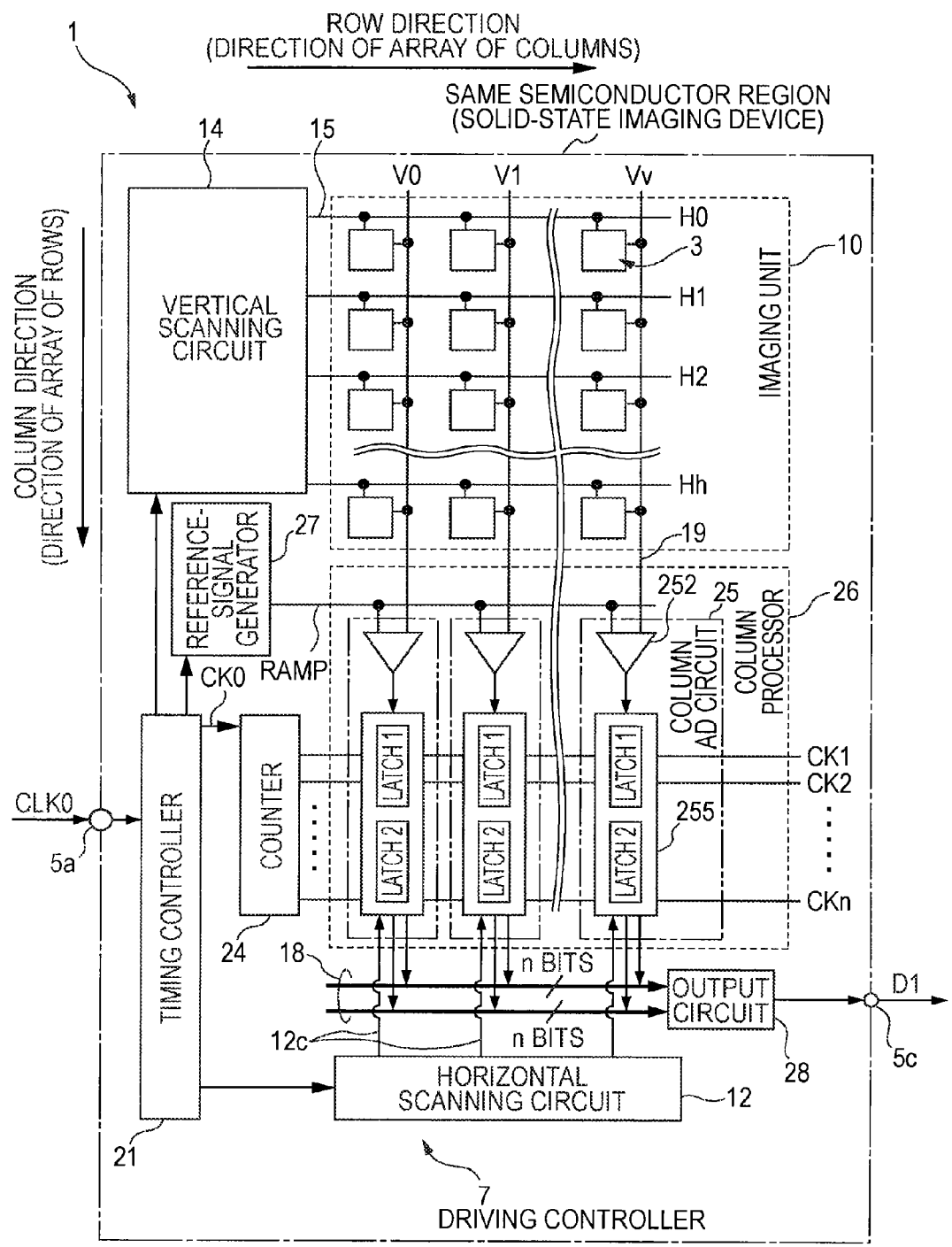
FIG. 21 is a schematic diagram showing a CMOS solid-state imaging device according to the related art, in which an AD converter and a pixel unit are mounted on the same semiconductor substrate.
Figure 22:
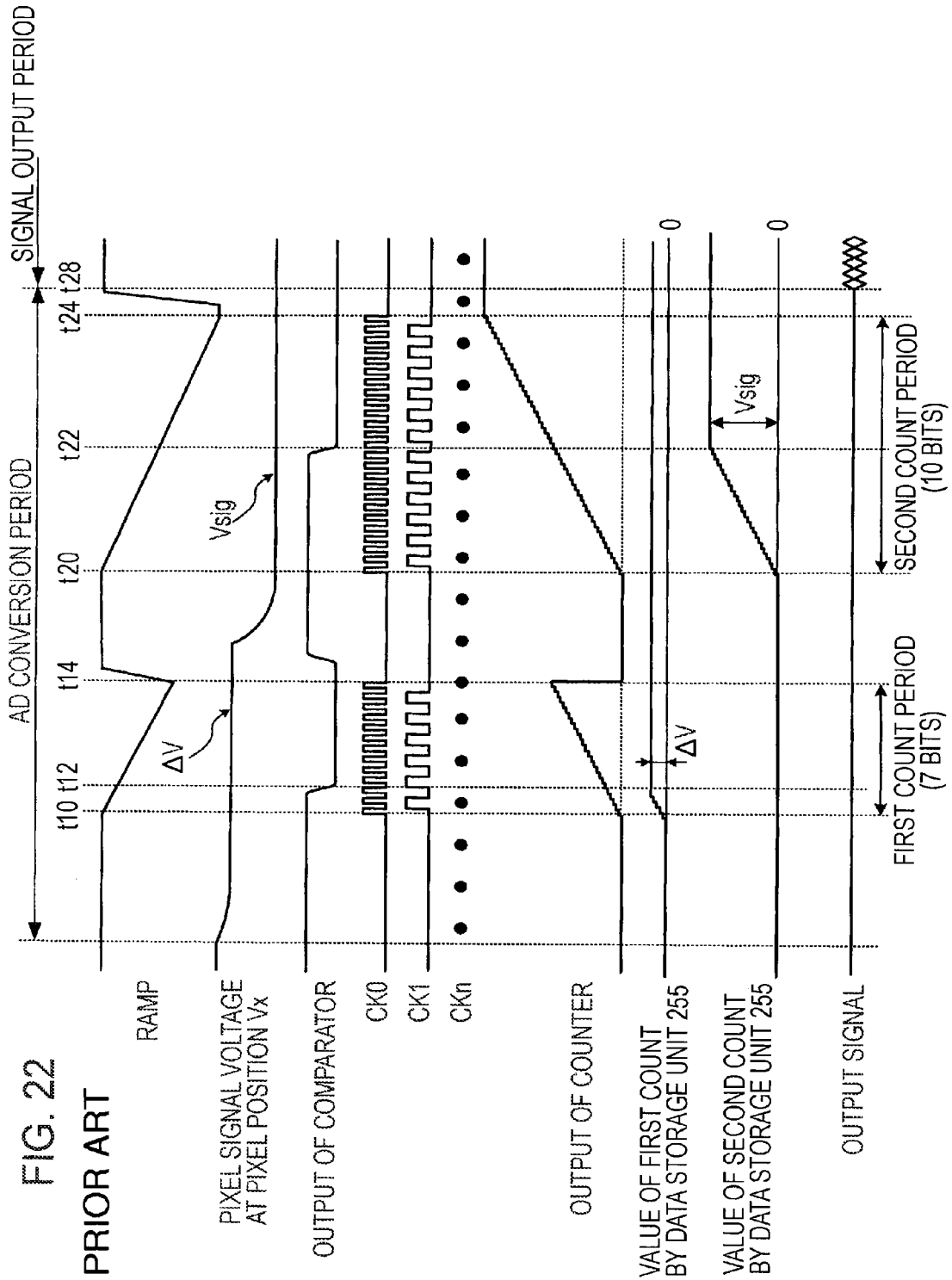
FIG. 22 is a timing chart for explaining an operation of the solid-state imaging device according to the related art shown in FIG. 21.

Although the construction of the counter 254 is not shown, the counter 254 can be implemented by changing the wiring of the data storage unit 255 formed by latches, shown in FIG. 21, into wiring for synchronous counter, and the counter 254 internally performs counting based on input of a single count clock CK0. The count clock CK0, similarly to the stairs-like voltage waveform, is generated based on a high-speed clock (e.g., a multiplied clock) supplied from the clock converter 23, so that the count clock CK0 can be faster than the master clock CLK0 input via the terminal 5a.

The n-bit counter 254 can be implemented by a combination of n latches, so that the circuitry scale is reduced to half compared with the data storage unit 255 formed by two lines of n latches shown in FIG. 21. Furthermore, the counter 24 is not needed, so that the overall size becomes considerably compact compared with the arrangement shown in FIG. 21.

As will be described later in detail, the counter 254 in the first embodiment uses a common up/down counter (U/D CNT) irrespective of counting mode, and is capable of switching between down-counting operation and up-counting operation (i.e., alternately).

Furthermore, the counter 254 in the first embodiment uses an asynchronous counter that outputs a count value asynchronously with the count clock CK0. More specifically, the counter circuit 400 according to the first embodiment described with reference to FIGS. 1 to 4 is used as a basic element.

In the case of a synchronous counter, operations of all flip-flops (elements of the counter) are restricted by the count clock CK0. On the other hand, in the case of an asynchronous counter, the operation limit frequency is determined only by the limiting frequency of the first flip-flop (element of the counter). Thus, when operation at a higher frequency is needed, preferably, an asynchronous counter is used as the counter 254.

The counter 254 receives control pulses from the horizontal scanning circuit 12 via the control line 12c. The counter 254 has a latch function for holding the result of counting, and it holds a count output value until an instruction by control pulses is received via the control line 12c.

As described earlier, the column AD circuits 25 constructed as described above are provided for the respective vertical signal lines 19 (V0, V1, ... ), forming the column processor 26, which is a column-parallel ADC block.

The outputs of the individual column AD circuits 25 are connected to the horizontal signal lines 18. As described earlier, the horizontal signal lines 18 includes n-bit signal lines corresponding to the bit width of the column AD circuits 25. The horizontal signal lines 18 are connected to the output circuit 28 via n sensing circuits (not shown) associated with the respective output lines.

In the construction described above, the column AD circuits 25 performs counting in a pixel-signal reading period, outputting the result of counting at specific timing. That is, first, the voltage comparator 252 compares the ramp waveform voltage supplied from the reference-signal generator 27 with the pixel-signal voltage input via the vertical signal line 19. When these voltages are equal, the output of the voltage comparator 252 is inverted (changes from H level to L level in this embodiment).

The counter 254 starts counting in down-count mode or up-count mode in synchronization with the ram waveform voltage generated by the reference-signal generator 27. When the counter 254 is notified of the inversion of the output of the comparator 252, the counter 254 stops counting, and latches a current count value as pixel data, whereby AD conversion is completed.

Then, the counter 254, by shift operations according to horizontal select signals CH(i) input via the control line 12c from the horizontal scanning circuit 12 at specific timing, outputs pixel data stored sequentially to the outside of the column processor 26 or to the outside of the chip of the pixel unit 10 via the output terminal 5c.

The solid-state imaging device 1 may include other various signal processing circuits, although such circuits are not shown since they are not directly relevant to the description of the embodiment.

First Example Configuration of Counter

Figure 12:
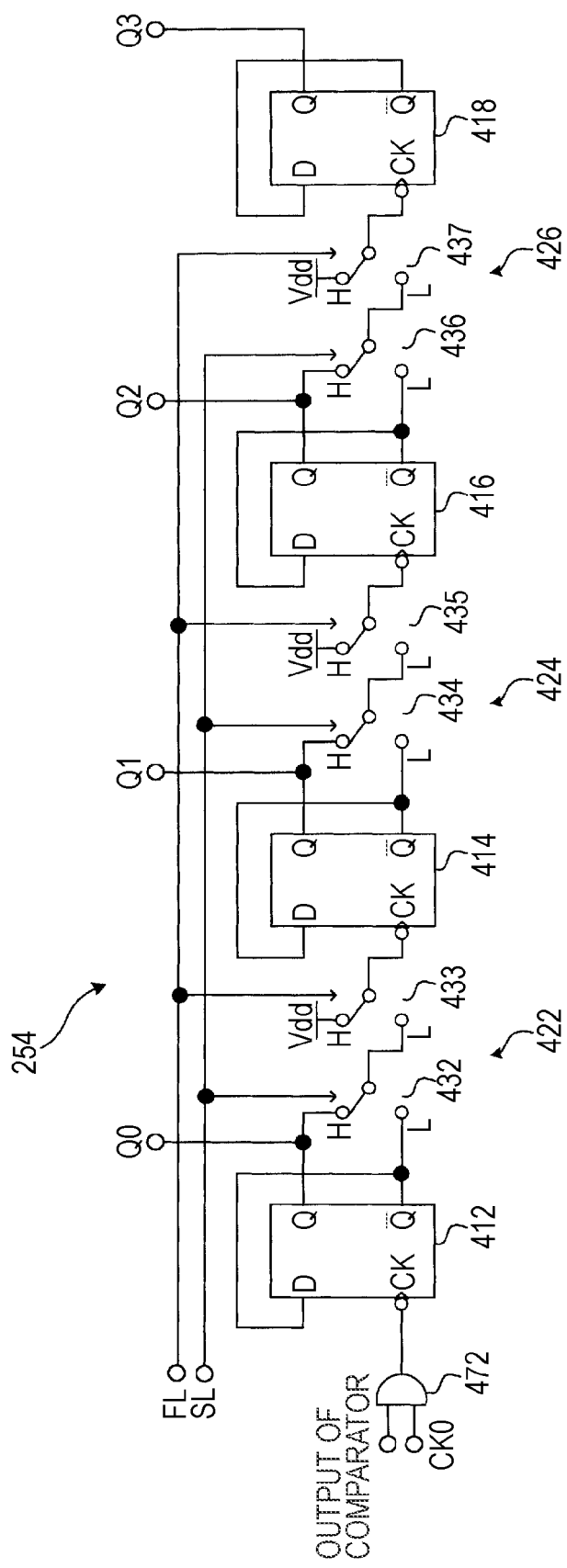
FIG. 12 is a block circuit diagram showing a first example configuration of a counter.

FIG. 12 is a block circuit diagram showing a first example configuration of the counter 254. In the first example, the basic configuration of asynchronous counter is the same as the counter circuit 400 according to the first embodiment described with reference to FIGS. 1 to 4. However, a gate circuit that controls input of a clock signal to the clock terminal CK of the first flip-flop 412 in the counter circuit 400 according to the first embodiment shown in FIG. 2, based on a result of comparison by the voltage comparator 252, is additionally provided.

More specifically, the counter 254 in the first example includes a two-input AND gate 472 whose output is connected to the clock terminal of the first flip-flop 412. One input terminal of the AND gate 472 receives input of a result of comparison by the voltage comparator 252, and the other input terminal receives input of the counter clock CK0 from the communication and timing controller 20.

Thus, the clock input to the clock terminal of the first flip-flop 412 is the logic product (AND) of the output of the voltage comparator 252 and the count clock CK0. Accordingly, it is possible to perform counting in accordance with a comparison period of the voltage comparator 252.

More specifically, the communication and timing controller 20, in order to activate generation of the reference signal RAMP by the reference-signal generator 27, supplies the control data CN4 and the count clock CK0 to the reference-signal generator 27. The reference-signal generator 27 starts counting in synchronization with the count clock CK0 from an initial value in accordance with the control data CN4, and generates a stairs-like ramp waveform by reducing voltage by a predetermined step size in each clock cycle, supplying the resulting reference signal RAMP to the voltage comparator 252.

The voltage comparator 252 searches for a point where the ramp-waveform reference signal RAMP matches a voltage corresponding to a reference component or a signal component of a pixel signal from a unit pixel 3, and pulls its output to Low level when a match is found.

The counter 254 commonly receives the counter clock CK0 supplied to the reference-signal generator 27. The AND gate 262 gates the counter clock CK0 by a comparison output supplied from the voltage comparator 252.

Thus, when the reference signal RAMP used for comparison becomes smaller than the voltage corresponding to the reference component or the signal component of the pixel signal, supply of the count clock to the first flip-flop 412 of the asynchronous counter 400 is stopped, so that counting is not performed further. Thus, a value that is finally written to each of the flip-flops 410 is a digital value representing the voltage corresponding to the reference component or the signal component of the pixel signal.

That is, the counter 254 performs counting based on the count clock CK0 from a time when the ramp-waveform reference signal RAMP used for comparison by the voltage comparator 252 is generated to a time when the reference signal RAMP matches a reference component or a signal component of a pixel signal, thereby obtaining digital data corresponding to the magnitude of the reference component or the signal component.

Second Example Configuration of Counter

Figure 13A:
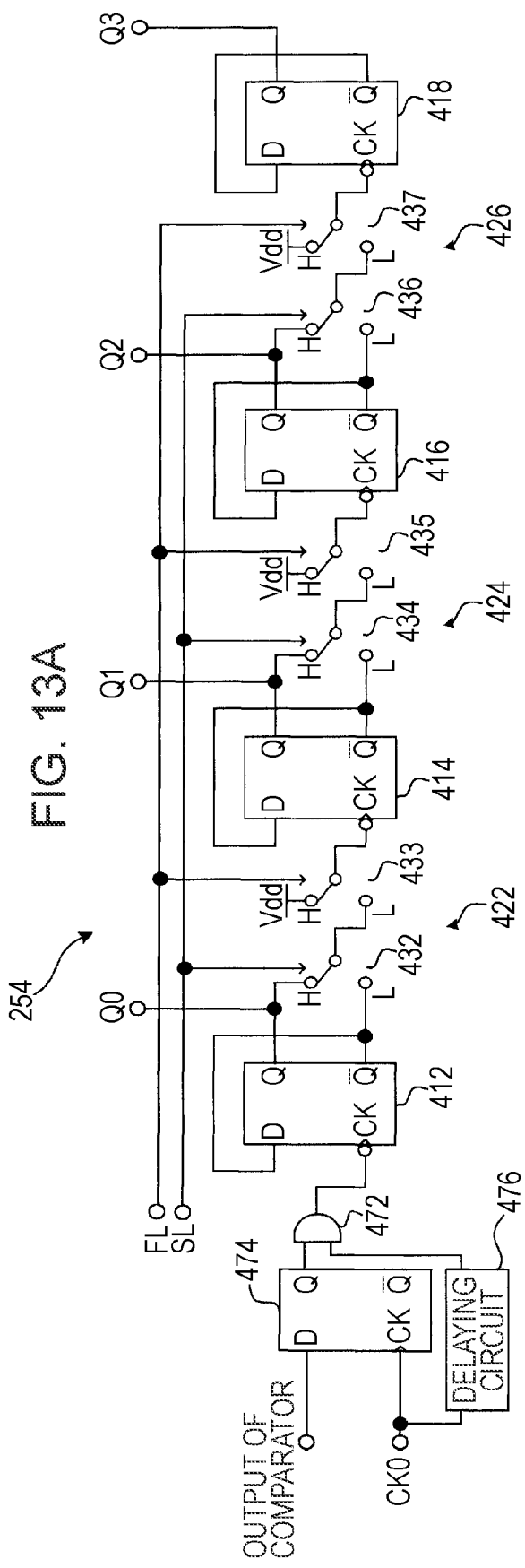
FIG. 13A is a block circuit diagram showing a second example configuration of a counter.
Figure 13B:
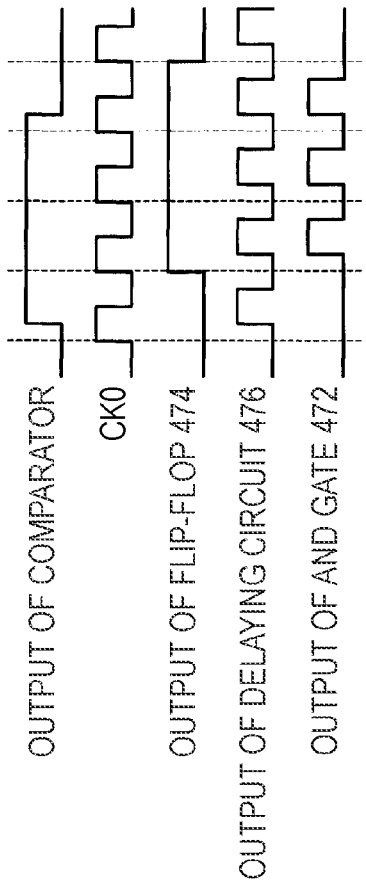
FIG. 13B is a timing chart for explaining an operation thereof.

FIG. 13A is a block circuit diagram showing a second example configuration of the counter 254, and FIG. 13B is a timing chart for explaining an operation thereof. In the second example, the basic configuration of asynchronous counter is the same as the counter circuit 400 according to the first embodiment shown in FIG. 2, similarly to the first example. However, at a previous stage of the AND gate 472 that controls input of clock signal to the clock terminal CK of the first flip-flop 412, a positive-edge D flip-flop 474 and a delaying circuit 476 are additionally provided.

It suffices for the delaying circuit 476 to delay the counter clock CK0 supplied from the communication and timing controller 20 by a predetermine period (e.g., one clock cycle), as shown in FIG. 13B. The delaying circuit 476 can be implemented by various known circuit configurations, for example, by using gate delay.

The D input terminal of the D flip-flop 474 receives a result of comparison by the voltage comparator 252. The clock terminal CK of the D flip-flop 474 receives the counter clock CK0 from the communication and timing controller 20. The non-inverting output Q of the D-flip-flop 474 is input to one input terminal of the AND gate 472. Thus, the D flip-flop 474 outputs the outputs of the voltage comparator 252 in synchronization with the rising edges of the counter clock CK0.

The other input terminal of the AND gate 472 receives the counter clock CK0 from the communication and timing controller 20 via the delaying circuit 476. The output of the AND gate 472 is connected to the clock terminal of the first flip-flop 412.

In the first example configuration, the AND gate 472 is used as a functional element that controls input of clock signal to the clock terminal CK of the first flip-flop 412. However, when such a simple AND gate is used, gridge or other noise due to timing deviation or the like could occur.

In contrast, by taking the logic product (AND) while synchronizing the comparator outputs with the edges (rising edges in this example) of the counter clock CK0 as in the second example, the results of comparison by the voltage comparator 252 can be captured by the clock terminal of the first flip-flop 412 in synchronization with the counter clock CK0. This is preferably since the effect of gridge or the like is alleviated.

Although the counter circuit 400 according to the first embodiment shown in FIG. 2 is used as the basic configuration of asynchronous counter in the counters 254 shown in FIG. 12 and FIG. 13A, similar up/down counters can be readily implemented using the counter circuits 400 and 500 according to the second and third embodiments.

First Embodiment of the Operation of the Solid-State Imaging Device

FIG. 14 is a diagram for explaining an operation of the column AD circuits 25 in the solid-state imaging device 1 according to the first embodiment shown in FIG. 11. As a mechanism for converting analog pixel signals sensed by the unit pixels 3 of the pixel unit 10 into digital signals, for example, a point where the ramp-waveform reference signal RAMP that decreases at a specific gradient matches the voltage of a reference component or signal component in pixel signals from the unit pixels 3. Then, counting is performed based on a count clock between the time when the reference signal RAMP used for comparison is generated and the time when the signal corresponding to a reference component or signal component in pixel signals matches the reference signal, whereby a count value corresponding to the magnitude of the reference component or signal component is obtained.

In a pixel signal output from the vertical signal line 19, a signal component Vsig appears after a reset component ΔV that serves as a reference component, including noise of the pixel signal. When the first iteration is performed for the reference component (reset component ΔV), the second iteration is performed for a signal including the signal component Vsig in addition to the reference component (reset component ΔV). Now, the operation will be described more specifically.

For the first iteration of reading, the communication and timing controller 20 resets the count value of the counter 254 to an initial value of "0", and causes the counter 254 to enter down-count mode by pulling the switching control signal SL to Low level. When the first iteration of reading from unit pixels 3 on an arbitrary row Hx to the vertical signal lines 19

(V0, V1, . . . ) becomes stable, the communication and timing controller 20 supplies control data CN4 for generating the reference signal RAMP to the reference-signal generator 27.

In response to the control data CN4, the reference-signal generator 27 inputs ramp waveform that temporally changes in a ramp-like manner as a comparison voltage to one input terminal RAMP of the voltage comparator 252. The voltage comparator 252 compares the RAMP waveform comparison voltage with a pixel signal voltage of a vertical signal line 19 (Vx) supplied from the pixel unit 10.

Simultaneously with the input of the reference signal RAMP to the input terminal RAMP of the voltage comparator 252, in order to measure a time of comparison by the voltage comparator 252 by the counter 254 provided for each row, in synchronization with the ramp waveform voltage generated by the reference-signal generator 27 (t10), a count clock CK0 is input from the communication and timing controller 20 to the clock terminal of the counter 254, and down-counting is started from an initial value of "0" as the first counting operation. That is, counting is started toward the negative direction.

The voltage comparator 252 compares the ramp reference signal RAMP supplied from the reference-signal generator 27 with the pixel signal voltage Vx input via the vertical signal line 19, and inverts its output from H level to L level when these voltages become equal (t12). That is, the voltage comparator 252 compares a voltage signal corresponding to a reset component Vrst with the reference signal RAMP, and generates an active-low (L) pulse signal after a time corresponding to the magnitude of the reset component Vrst elapses, outputting the pulse signal to the counter 254.

In response to the pulse signal, the counter 254 stops counting substantially at the same time as the inversion of the output of the voltage comparator 252, and latches a current count value as pixel data, whereby AD conversion is completed (t12). That is, the counter 254 starts down-counting at the time of generation of the ramp reference signal RAMP supplied to the voltage comparator 252, and continues counting based on the clock CK0 until an active-low (L) pulse signal is obtained by comparison, thereby obtaining a count value corresponding to the magnitude of the reset component Vrst.

The communication and timing controller 20, when a predetermined down-counting period elapses (t14), stops supply of control data to the voltage comparator 252 and supply of the count clock CK0 to the counter 254. Thus, the voltage comparator 252 stops generating the ramp reference signal RAMP.

In the first iteration of reading, counting is performed by detecting the reset level Vrst in the pixel signal voltage Vx by the voltage comparator, i.e., the reset component $\Delta V$ of a unit pixel 3 is read.

In the reset component $\Delta V$, noise that varies among the unit pixels 3 is included as offset. Generally, however, variation of the reset component $\Delta V$ is small, and the reset level Vrst is substantially the same for all the pixels, so that the output value of the reset component $\Delta V$ on an arbitrary vertical signal line 19 is substantially known.

Thus, in the first operation of reading the reset component $\Delta V$, it is possible to shorten the down-count period (comparison period t10 to t14) by adjusting the ramp voltage. In this embodiment, the maximum period of comparison for the reset component $\Delta V$ is a count period corresponding to 7 bits (128 clock cycles).

In the second reading operation, in addition to the reset component $\Delta V$, a signal component Vsig corresponding to the amount of incident light for each unit pixel 3 is read, and the same operation as the first reading operation is performed.

More specifically, the communication and timing controller 20 first pulls the switching control signal SL to High level so that the counter 254 enters the up-count mode (t16).

As described earlier, when switching between the down-count mode to the up-count mode occurs, the count value becomes broken, failing to maintain the continuity of count value. That is, it is not possible to perform down-counting and up-counting while maintaining the count value before and after the switching.

Thus, before supplying the count clock CK0 for starting comparison and counting in the up-count mode, an active-H one-shot pulse is supplied to the counter 254 as the switching control signal FL (t17 to t18). Thus, the clock terminals of the flip-flops 410 constituting the asynchronous counter 254 are once forcibly pulsed to High level and are then returns to the status after the mode switching. Thus, as described earlier, the count value changed at the time of switching from down-counting to up-counting is restored to the original count value.

Then, when the second operation of reading from unit pixels 3 of an arbitrary line Hx to the vertical signal lines 19 (V0, V1, . . . ) becomes stable, the communication and timing controller 20 supplies control data CN4 for generating the reference-signal RAMP to the reference-signal generator 27 together with the clock CK0.

In response to the control data CN4, the reference-signal generator 27 inputs a ramp waveform that temporally changes in a ramp-like manner as a comparison voltage to the one input terminal RAMP of the voltage comparator 252. The voltage comparator 252 compares the ramp waveform comparison voltage (reference signal RAMP) with a pixel signal voltage of an arbitrary vertical signal line 19 (Vx) supplied from the pixel unit 10.

Simultaneously with the input of the reference signal RAMP to the input terminal RAMP of the voltage comparator 252, in order to measure a comparison time of the voltage comparator 252 by the counter 254 provided for each row, in synchronization with the ramp waveform voltage generated by the reference-signal generator 27 (t20), the communication and timing controller 20 inputs a count clock CK0 to the clock terminal of the counter 254. Then, as the second counting operation, as opposed to the first counting operation, up-counting is started from a count value corresponding to the reset component $\Delta V$ of the unit pixel 3 obtained in the first reading operation. That is, counting is started in the positive direction.

The voltage comparator 252 compares a pixel signal voltage Vx input via a vertical signal line 19 with the ramp reference signal RAMP supplied from the reference-signal generator 27. When these voltages become equal, the voltage comparator 252 inverts its output from H level to L level (t22). That is, the voltage comparator 252 compares a voltage signal corresponding to the signal component Vsig with the reference signal RAMP, generates an active-low (L) pulse signal after a time corresponding to the magnitude of the signal component Vsig elapses, and supplies the pulse signal to the counter 254.

Substantially at the same time with the inversion of the output of the voltage comparator 252, the counter 254 stops counting and latches a current count value as pixel data, whereby AD conversion is finished (t22). That is, the counter 254 starts down-counting when generation of the ramp reference signal RAMP supplied to the voltage comparator 252 is started, and continues counting based on the clock CK0 until an active-low (L) pulse signal is obtained by comparison, thereby obtaining a count value corresponding to the magnitude of the signal component Vsig.

The communication and timing controller 20, when a predetermined down-counting period elapses (t24), stops supply of control data to the voltage comparator 252 and supply of the count clock CK0 to the counter 254. Thus, the voltage comparator 252 stops generating the ramp reference signal RAMP.

In the second reading operation, counting is performed while detecting the signal component Vsig of the pixel signal voltage Vx by the voltage comparator 252, so that the signal component Vsig of the unit pixel 3 is read.

In this embodiment, the counter 254 performs down-counting in the first reading operation and up-counting in the second reading operation. Thus, the counter 254 automatically performs subtraction according to expression (1) below, holding a count value in accordance with the result of subtraction.

(Count value in the second comparison period)–
(Count value in the first comparison period)   (1)

Expression (1) can be rearranged as expression (2), so that the count value held by the counter 254 corresponds to the signal component Vsig.

(Second comparison period)–(First comparison period)=(Signal component Vsig+reset component $\Delta V$+offset component of column AD circuit 25)–(reset component $\Delta V$+offset component of column AD circuit 25)=(Signal component Vsig)   (2)

That is, as described above, by the subtraction in the counter 254 through the two reading and counting operations, i.e., down-counting in the first reading operation and up-counting in the second reading operation, the reset component $\Delta V$ including variation for each unit pixel 3 and the offset component for each column AD circuit 25 can be removed. Thus, only the signal component Vsig corresponding to the amount of incident light for each unit pixel 3 can be extracted by a simple configuration. At this time, advantageously, reset noise can also be removed.

Thus, the column AD circuit 25 in this embodiment operates as a correlated double sampling (CDS) processing unit as well as an AD converter that converts analog pixel signals into digital pixel data.

Furthermore, since pixel data represented by the count value according to expression (2) represents a positive signal voltage, complement operation is not needed, so that compatibility with existing systems is high.

In the second reading operation, the signal component Vsig corresponding to the amount of incident light is read. Thus, in order to allow determining the amount of light in a large range, a long up-counting period (t20 to t24, comparison) period must be provided, considerably changing the ramp voltage supplied to the voltage comparator 252.

Thus, in this embodiment, the maximum period of comparison for the signal component Vsig is chosen to be a count period corresponding to 10 bits (1024 clock cycles). That is, the maximum period of comparison for the reset component $\Delta V$ (reference component) is chosen to be shorter than that for the signal component Vsig. Instead of choosing the same maximum period of comparison, i.e., maximum period of AD conversion, for the reset component $\Delta V$ (reference component) and the signal component Vsig, the maximum period of comparison for the reset component $\Delta V$ (reference component) is chosen to be shorter than that for the signal component Vsig, so that the total AD conversion period over the two iterations becomes shorter.

In this case, the number of bits of comparison differs between the first iteration and the second iteration. However, by supplying control data from the communication and timing controller 20 to the reference-signal generator 27 and causing the reference-signal generator 27 to generate the ramp voltage based on the control data, the gradient of the ramp voltage, i.e., the rate of change in the reference signal RAMP, is maintained the same between the first iteration and the second iteration. Since the ramp voltage is generated by digital control, it is easy to maintain the same gradient of ramp voltage between the first iteration and the second iteration. Thus, it is possible to equalize the precision of AD conversion, so that a correct result of subtraction according to expression (1) is obtained by the up/down counter.

At a specific timing (t28) after the second counting operation is finished, the communication and timing controller 20 instructs the horizontal scanning circuit 12 to read pixel data. In response to the instruction, the horizontal scanning circuit 12 sequentially shifts the horizontal select signal CH(i) supplied to the counter 254 via the control line 12c.

Accordingly, the count value according to expression (2), held by the counter 254, i.e., pixel data represented by n-bit digital data, is sequentially output from the output terminal 5c to the outside of the column processor 26 or to the outside of the chip including the pixel unit 10 via the n horizontal signal lines 18. Then, similar operation is repeated for each row, whereby video data D1 representing a two-dimensional image is obtained.

As described above, according to the solid-state imaging device of the first embodiment, two counting operations are performed using an asynchronous up/down counter while switching processing mode of the up/down counter. Furthermore, in an arrangement including a matrix of unit pixels 3, column-parallel AD circuits are provided, i.e., column AD circuits 25 are provided for the respective columns.

Since an asynchronous counter is used, the limiting operating frequency is determined only by the limiting frequency of the first flip-flop, so that high-speed operation is allowed. Even when a difference signal component between a reference component and a signal component is converted into digital data by performing AD conversion in two iterations, AD conversion as a whole can be executed quickly, and the AD conversion period can be shortened.

Furthermore, it is possible to directly subtract a reference component (reset component) from a signal component for each column as a result of the second counting operation. Thus, memories for holding the results of counting associated with the reference component and the signal component can be implemented by a latch function of the counter. Therefore, special memories for holding data obtained by AD conversion need not be provided separately from the counter.

Furthermore, a special subtractor for subtracting the reference component from the signal component is not needed. Thus, compared with the related art, circuitry scale or circuit area can be reduced. Furthermore, increase in noise, increase in current, or increase in power consumption can be avoided.

Furthermore, since the column AD circuit includes a comparator and a counter, irrespective of the number of bits, counting can be controlled by a single count clock for the operation of the counter and a control line for switching count mode. Thus, signal lines for leading count values of counters to memories, needed in the related art, are not needed. This serves to avoid increase in noise or increase in power consumption.

That is, in the solid-state imaging device 1 having an AD converter on the same chip, a column AD circuit 25 that acts as an AD converter is implemented by a pair of the voltage comparator 252 and the counter 254, the counter 254 performs down-counting and up-counting in combination, and the difference between a basic component (reset component in this embodiment) and a signal component of a signal subject to processing is converted into digital data. This serves to avoid problems relating to circuitry scale, circuit area, power consumption, the number of wires for interfacing with other functional units, or noise or consumption current associated with the wires.

Second Embodiment of the Construction of Solid-State Imaging Device

Figure 15:
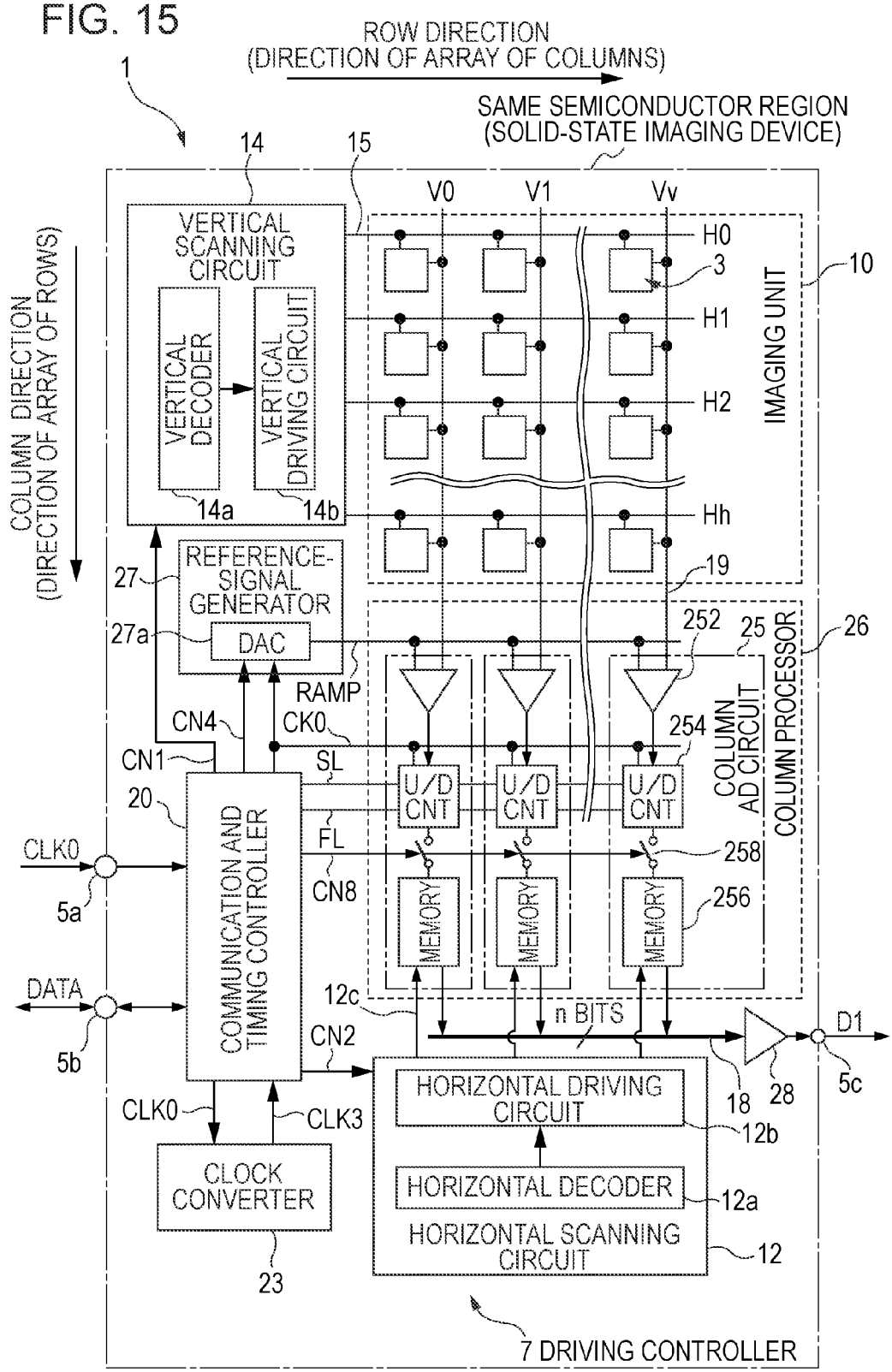
FIG. 15 is a schematic diagram showing the construction of a CMOS solid-state imaging device according to a second embodiment of the present invention.

FIG. 15 is a schematic diagram showing the construction of a CMOS solid-state imaging device (CMOS image sensor) according to a second embodiment of the present invention. In a solid-state imaging device 1 according to the second embodiment, compared with the solid-state imaging device 1 according to the first embodiment, the construction of column AD circuits 25 is modified.

In a column AD circuit 25 in the second embodiment, at a subsequent stage of a counter 254, a data storage unit 256 that functions as an n-bit memory for holding the result of counting by the counter 254, and a switch 258 disposed between the counter 254 and the data storage unit 256 are provided.

The switch 258 receives a memory transfer instruction pulse CN8 as a control pulse at a specific timing from the communication and timing controller 20, commonly with the switches 258 of the other columns. Upon receiving the memory transfer instruction pulse CN8, the switch 258 transfers a count value of the associated counter 254 to the data storage unit 256. The data storage unit 256 stores the count value transferred.

The scheme for storing the count value of the counter 254 in the data storage unit 256 at a specific timing is not limited to providing the switch 258 therebetween. For example, the counter 254 and the data storage unit 256 may be directly connected to each other while controlling an output enable terminal of the counter 254 by the memory transfer instruction pulse CN8. Alternatively, the memory transfer instruction pulse CN8 may be used as a latch clock that determines timing for the data storage unit 256 to capture data.

The data storage unit 256 receives a control pulse from the horizontal scanning circuit 12 via a control line 12c. The data storage unit 256 holds the count value received from the counter 254 until an instruction by a control pulse is received via the control line 12c.

The horizontal scanning circuit 12 has a function of a reading scanner that reads the count values held by the respective data storage units 256 concurrently with the respective voltage comparators 252 and counters 254 of the column processor 26 performing their respective operations.

According to the construction of the second embodiment described above, it is possible to transfer the result of counting held by the counter 254 to the data storage unit 256. Thus, it is possible to control counting by the counter 254, i.e., AD conversion, and the operation of reading the result of counting to the horizontal signal line 18 independently of each other. This allows AD conversion and an operation of reading signals to the outside to be performed concurrently by a pipeline operation.

Second Embodiment of the Operation of Solid-State Imaging Device

Figure 16:
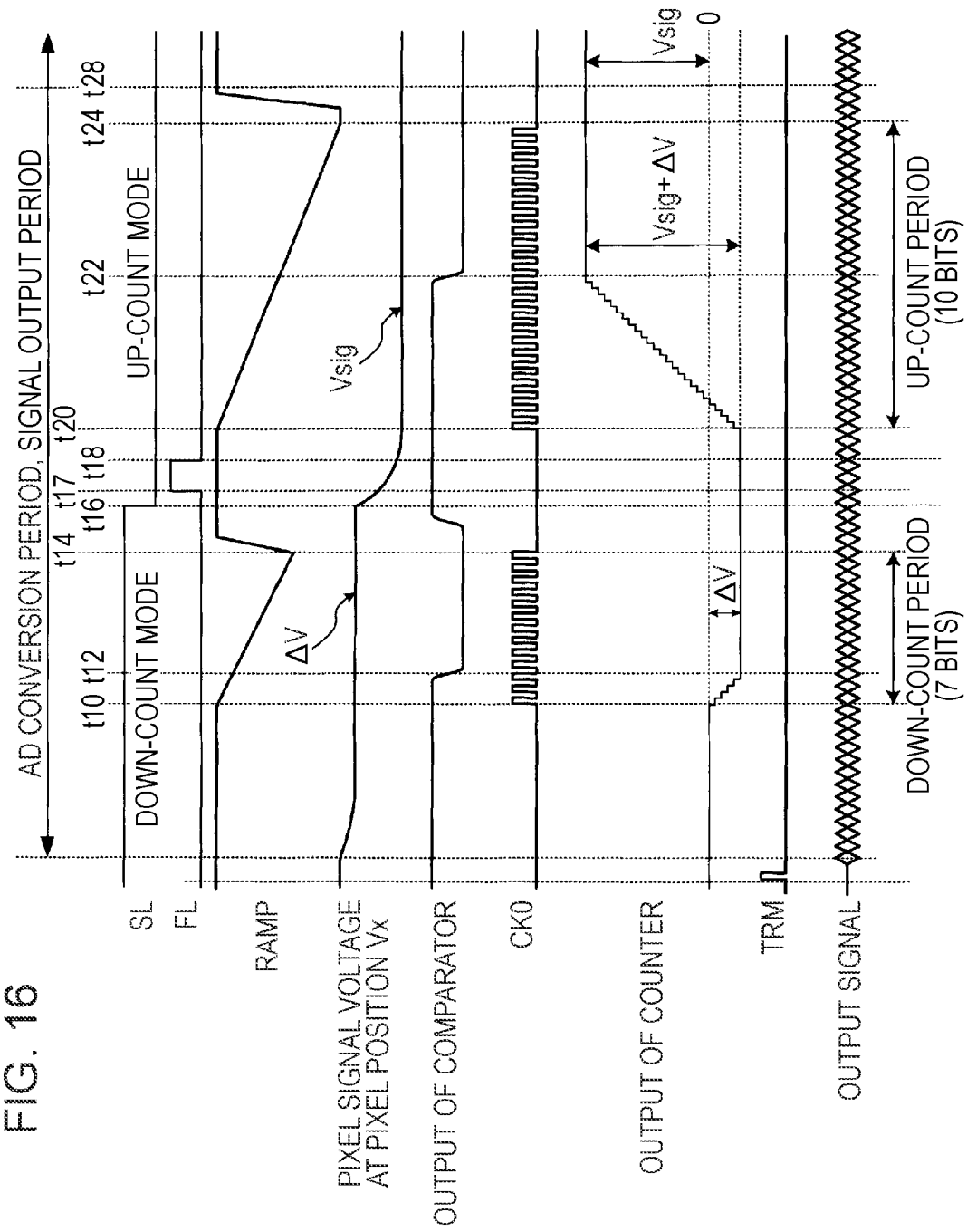
FIG. 16 is a timing chart for explaining an operation of a column AD circuit of the solid-state imaging device according to the second embodiment shown in FIG. 15.

FIG. 16 is a timing chart for explaining the operation of the column AD circuits 25 in the solid-state imaging device 1 according to the second embodiment shown in FIG. 15. AD conversion in the column AD circuits 25 is performed in the same manner as in the first embodiment, so that detailed description thereof will be omitted.

In the second embodiment, the data storage units 256 are added to the construction of the first embodiment. The basic operations including AD conversion are the same as those in the first embodiment. However, before the operation of the counter 254 (t30), based on a memory transfer instruction pulse CN8 from the communication and timing controller 20, the results of counting associated with a previous row Hx−1 is transferred to the data storage units 256.

According to the first embodiment, it is possible to output pixel data to the outside of the column processor 26 only after the second reading operation, i.e., AD conversion, is finished, so that the reading operation is restricted. In contrast, according to the second embodiment, count values representing the previous results of subtraction are transferred to the data storage units 256 before the first reading operation (AD conversion), so that the reading operation is not restricted.

Accordingly, the operation of outputting signals to the outside from the data storage units 256 via the horizontal signal line 18 and the output circuit 28 and the operation of reading signals from a current row Hx and counting by the counters 254 can be performed concurrently, allowing more efficient signal output.

Although the embodiments of the present invention have been described above, the scope of the present invention is not limited to the embodiments. Various modifications or improvements of the embodiments are possible without departing from the spirit of the present invention, and the modifications and improvements are included in the scope of the present invention.

The embodiments described above are not intended to limit the claims, and all the features of the embodiments are not necessarily needed. The embodiments described above include various phases of invention, and various aspects of the present invention can be extracted by appropriately combining the features described. Even if some features of the embodiments are removed, an arrangement including the remaining features can be extracted as an aspect of the present invention as long as similar advantages can be achieved.

For example, in the embodiments described above, in order to restore a count value changed at a time of switching count mode to an original count value, the clock terminals of flip-flops (latches) as basic elements of a counter are once forcibly pulled to High level (in the case of negative edges) or Low level (in the case of positive edges) and then returned to the status after the mode switching. However, the scheme for restoring a count value changed at a time of switching count mode to an original value is not limited to the scheme described above.

Figure 17:
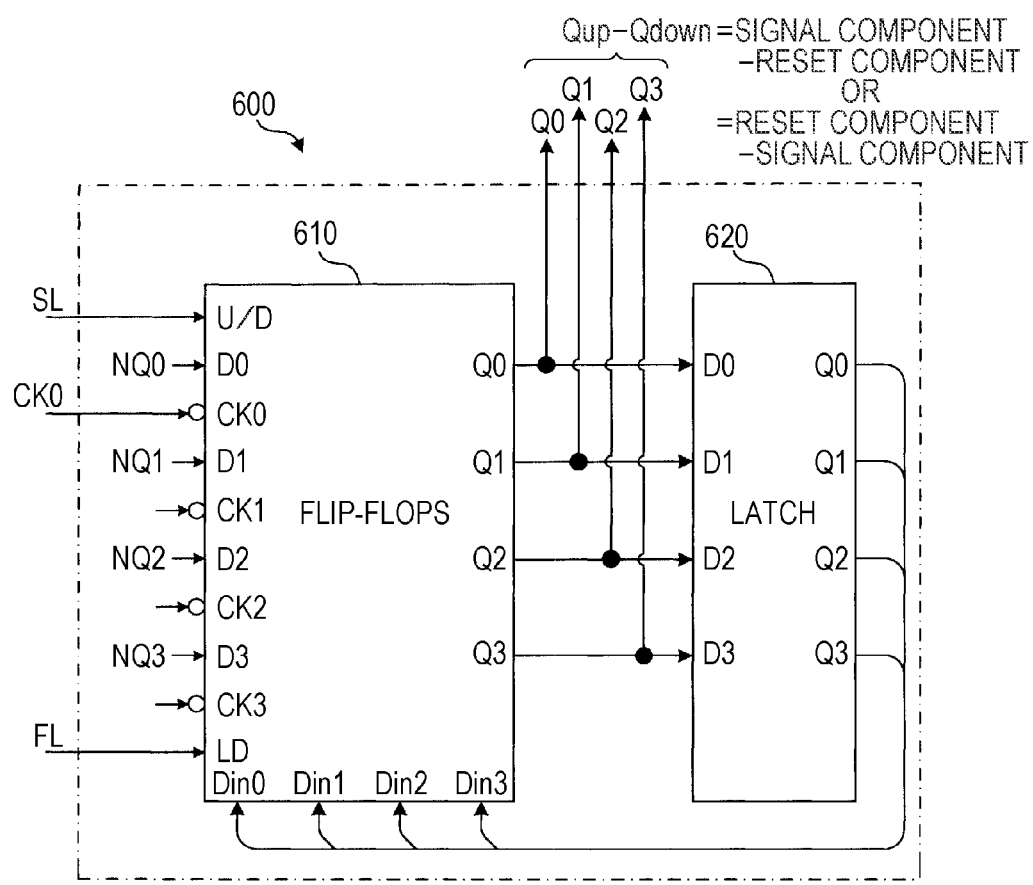
FIG. 17 is a diagram showing another example of arrangement for restoring a count value at a time of switching count mode.
Figure 18:
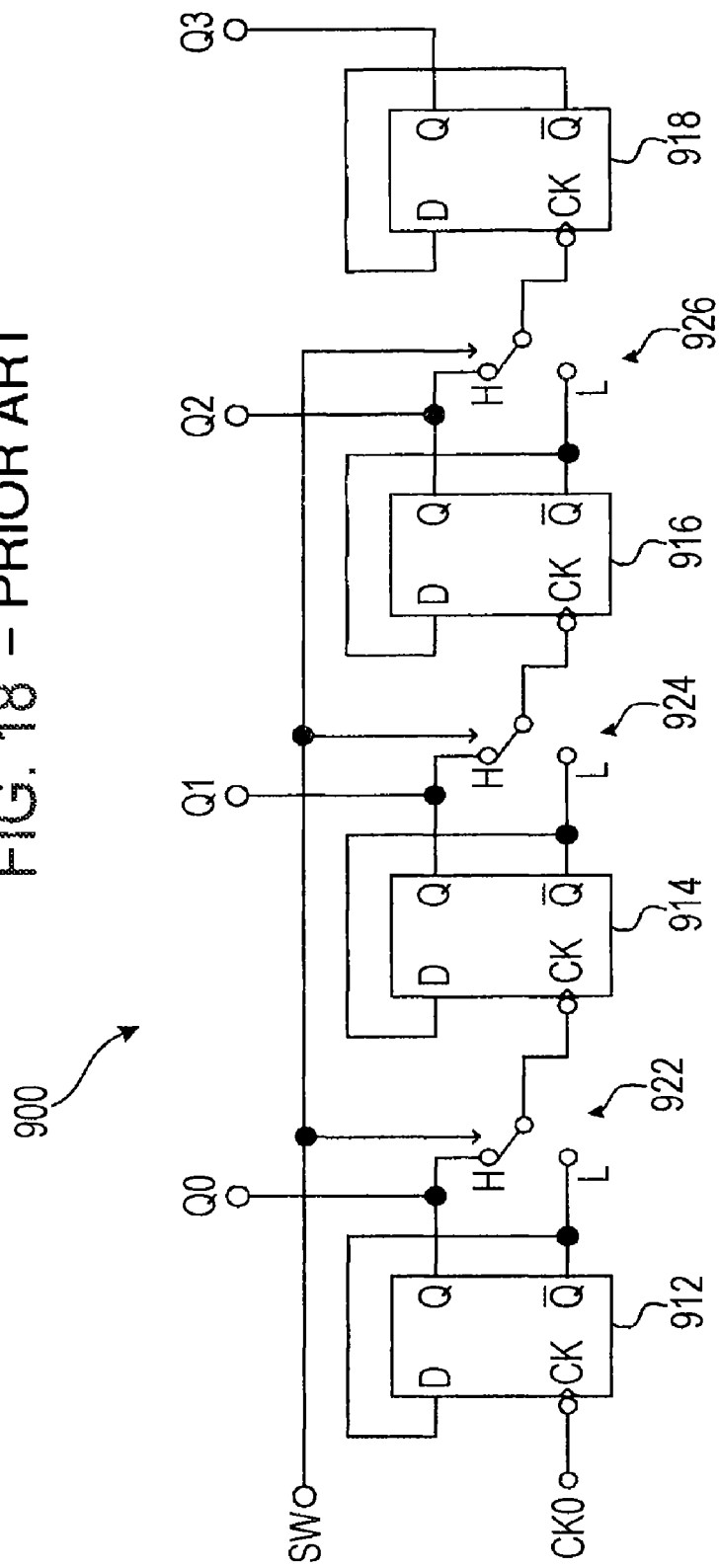
FIG. 18 is a diagram showing an example of asynchronous counter according to the related art, which is capable of switching mode.
Figure 19:
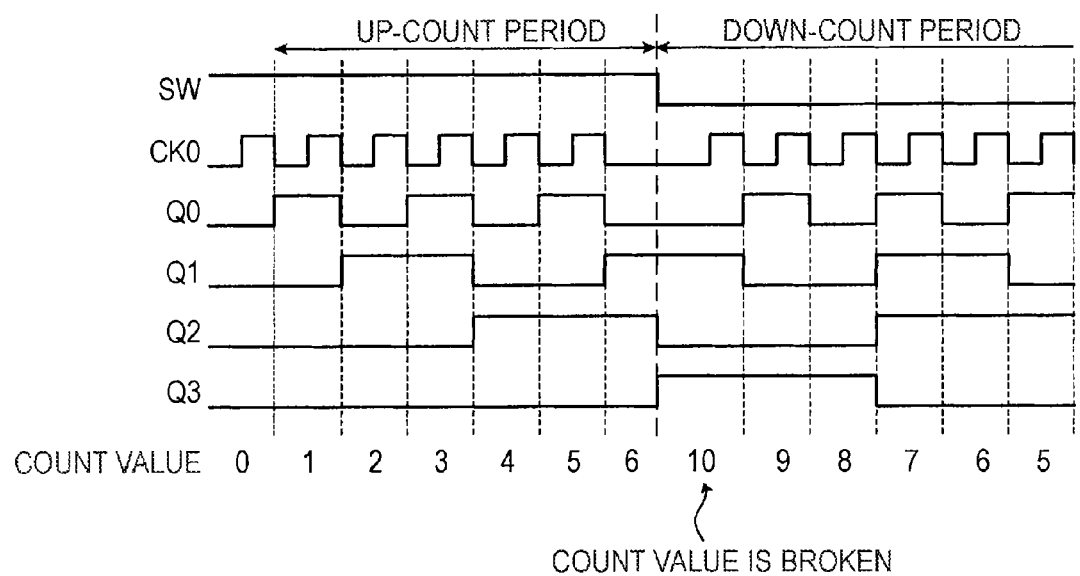
FIG. 19 is a timing chart for explaining an operation of the counter circuit shown in FIG. 18.
Figure 20:
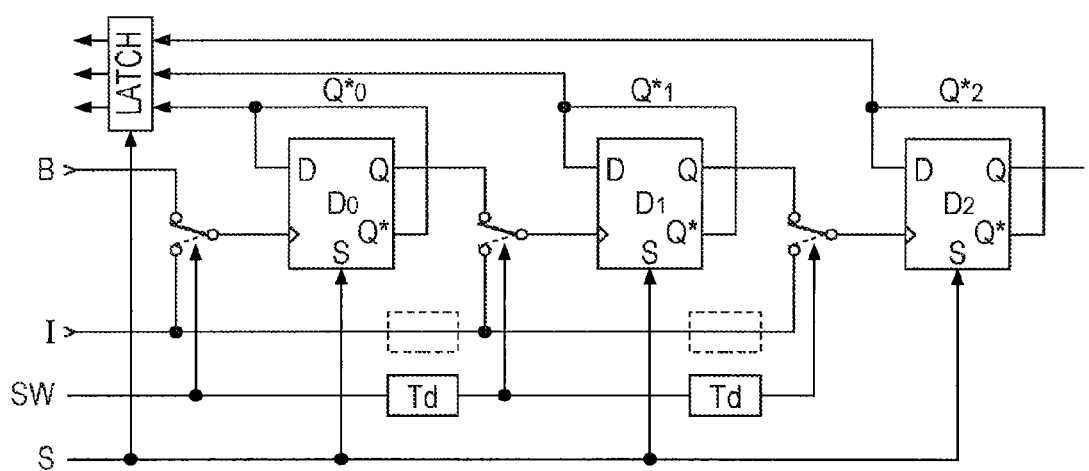
FIG. 20 is a diagram showing an arrangement proposed in the second patent document.

FIG. 17 shows another example arrangement for restoring a count value broken at a time of switching count mode to an original count value. As the basic configuration of an asynchronous counter, a counter circuit 600 is configured so that an arbitrary initial value can be loaded using known techniques.

For example, the counter circuit 600 includes flip flops 610 and latches 620. The example shown in FIG. 17 deals with 4-bit data.

The inverting outputs NQn of the flip-clops 610 constituting the asynchronous counter circuit 600 are connected to the D terminals (D0 to D3) of the flip-flops 610. Furthermore, the non-inverting outputs Qn of the flip-flops 610 constituting the asynchronous counter circuit 600 are input to the D terminals (D0 to D3) of the latches 620 (four latches in FIG. 17). The non-inverting outputs of the latches 620 are input to data setting terminals Din0 to Din3 of the associated flip-flops 610.

The non-inverting outputs Qn of the flip-flops 610 constituting the asynchronous counter are latched by the latches 620 (four latches in FIG. 17) based on associated clocks CKx so that states previous by one clock cycle are held. The associated clocks CKx refer to clocks input to the clock terminals of the individual flip-flops 610. Depending on count mode, the non-inverting output or the inverting output of the previous flip-flop is used.

By inputting the switching control signal FL to the load terminals LD of the flip-flops 610 after switching count mode by the switching control signal SL, data held by the latches 620 is written to the flip-flops 610, i.e., initial values are set. Thus, a count value immediately before the count value is changed at a time of switching count mode is set to the flip-flops 610. That is, the count value immediately before the count value is changed at the time of switching count mode is restored. Thus, the count value before switching count mode can be maintained, so that it is possible to continue counting while maintaining the continuity of count value after mode switching.

Accordingly, it is possible to directly subtract a reference component from a signal component, so that a special subtractor circuit for subtracting a reference component from a signal component is not needed. Furthermore, data need not be transferred to a subtractor. This serves to avoid increase in noise, increase in current, or increase in power consumption.

Furthermore, although edge-triggered flip-flops are used in the embodiments described above, alternatively, level-triggered flip-flops may be used.

Furthermore, although the column AD circuit 25 including the voltage comparator 252 and the counter 254 is provided for each column and signals are converted into digital data on a column-by-column basis in the embodiments described above, without limitation to the arrangement described above, a single column AD circuit 25 may be provided for a plurality of columns with a switching circuit for switching among the columns.

Furthermore, although an AD conversion function is implemented in a column region provided on the reading side of the pixel unit 10, an AD conversion function may be implemented in other regions. For example, pixel signals are output in analog up to the horizontal signal line 18, and the pixel signals are then AD-converted before being passed to the output circuit 28.

Even in this case, when a signal subject to processing including a reference component and a signal component is compared with a reference signal for AD conversion, concurrently with the comparison, counting is performed in a down-count mode or an up-count mode, holding a count value at a time of completion of the comparison, by switching counting mode according to whether comparison is being performed for the reference component or the signal component, it is possible to obtain digital data representing the difference between the reference component and the signal component as results of performing counting in the down-count mode and in the up-count mode.

Thus, memories for holding the results of counting associated with the reference component and the signal component can be implemented by a latch function of the counter, so that special memories for holding data obtained by AD conversion needed not be provided separately from the counter. It suffices to provide a single AD converter for all the columns. Although high-speed conversion is needed, circuitry scale is reduced compared with the embodiments described above.

Furthermore, in the embodiments described above, in a pixel signal of a pixel, a signal component Vsig appears temporally after a reset component $\Delta V$ (reference component), and a processor at a subsequent stage processes a signal of positive polarity (the positive value becomes larger as the signal level becomes larger). In the first processing iteration, comparison and down-counting are performed for the reset component $\Delta V$ (reference component), and in the second processing iteration, comparison and up-counting are performed for the signal component Vsig. However, irrespective of the temporal order of the reference component and the signal component, combination and processing order of components and count modes are arbitrary. Depending on the processing order, digital data obtained in the second iteration becomes a negative value, in which case correction is performed or other suitable measure is taken.

Obviously, when the device architecture of the pixel unit 10 is such that the reset component $\Delta V$ (reference component) must be read after the signal component Vsig and a processor at a subsequent stage handles signals of positive polarity, it is efficient to perform comparison and down-counting for the signal component Vsig in the first processing iteration and to perform comparison and up-counting for the reset component $\Delta V$ (reference component) in the second processing iteration.

Furthermore, although the embodiments have been described in the context of a sensor including NMOS unit pixels as an example, without limitation to the example, the same operations and advantages as in the embodiments described above can be achieved for a sensor including PMOS unit pixels by considering the potential relationship as reversed (considering the polarities of potential as reversed).

Furthermore, although the embodiments have been described in the context of a CMOS sensor including a pixel unit that generates signal charges in response to light received as an example of solid-state imaging device that is capable of arbitrarily selecting and reading signals from individual unit pixels by address control, signal charges may be generated in response to electromagnetic waves in general, such as infrared rays, ultraviolet rays, or X rays, without limitation to light. The features of the embodiments described above can be applied to a semiconductor device including a large number of unit elements that output analog signals corresponding to electromagnetic waves received.

The embodiments have been described in the context of an example where an AD converter (column AD circuits in the example described above) including a comparator that compares a signal corresponding to a reference component and a signal corresponding to a signal component with a reference signal for AD conversion and a counter that performs counting in a down-count mode or an up-count mode using an asynchronous counter and holds a count value at a time of completion of the comparison in the comparator. However, the scheme of AD conversion in the embodiments described above may be applied to any electronic apparatus employing AD conversion for converting a difference signal component between two signal components, without limitation to a solid-state imaging device.

For example, by performing AD conversion outside the solid-state imaging device 1 using the comparator and the counter based on analog pixel signals captured from the solid-state imaging device 1, an electronic apparatus that obtains digital data (pixel data) of a true signal component and that performs desired digital signal processing based on the pixel data can be constructed.

Furthermore, the AD converter described in relation to the embodiments need not necessarily be provided as included in a solid-state imaging device or an electronic apparatus, and may be provided as an independent device in the form of an integrated circuit (IC) or an AD conversion module.

In this case, although the AD converter including the comparator and the asynchronous counter may be provided, an IC in which a reference-signal generator that generates the reference signal for AD conversion and supplies it to the comparator and a controller that switching counting mode in the counter according to whether the comparator is performing comparison for the reference component or the signal component is provided on the same semiconductor substrate, or a module including a combination of discrete chips, may be provided.

Figure 23:
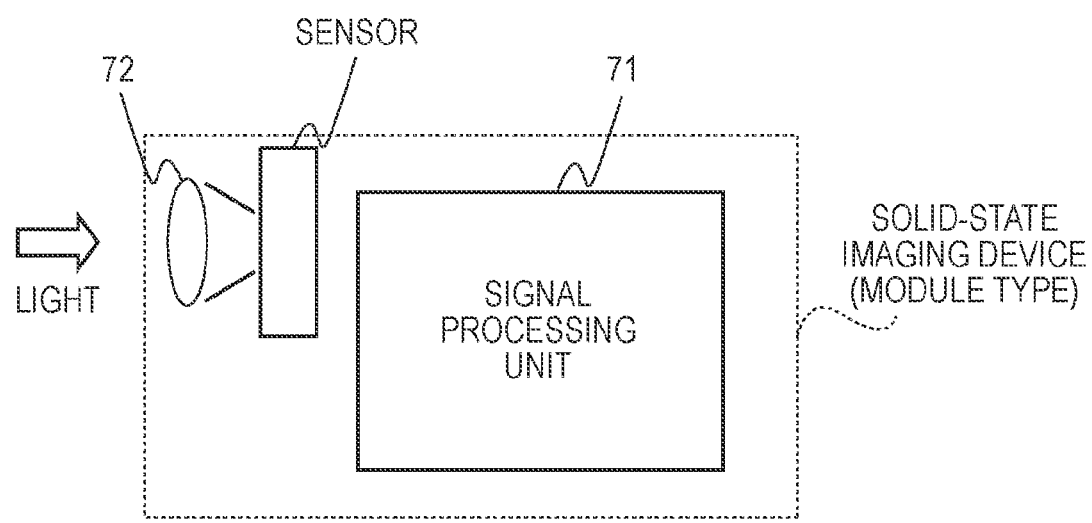
FIG. 23 is a block diagram of an imaging device of module type of this invention.

The imaging device of this invention may have other structures, in addition to the structures shown in FIG. 11. FIG. 23 is a block diagram of an imaging device of module type of this invention, which includes a signal processing unit 71 processing output signals and optical system 72.

Accordingly, functional units that are needed to control the operations of the comparator and the asynchronous counter can be handled in an integrated manner, facilitating handling and management of parts. Furthermore, since elements needed for AD conversion are integrated in the form of an IC or a module, manufacturing of a finished product of a solid-state imaging device or an electronic apparatus is facilitated.

What is claimed is:

1. An asynchronous counter circuit that is allowed to selectively perform counting in an up-count mode or counting in a down-count mode, the counter circuit comprising:
a counter processor configured so that when switching between the count modes occurs, a running count value is broken and there is an interval between count modes and when a mode begins the running count value is reset to the value before the running count value was broken.

2. The counter circuit according to claim 1, wherein a plurality of flip flops as basic elements of the counter is cascaded with each other, and said counter processor controls that clock terminals of said flip flops switches power supply level or ground level when said count value before switching of count mode are switched from count value converted by said count mode by said second control signal.

3. The counter circuit according to claim 2, further comprising an initial-stage clock switch that switches the polarity of a counter clock supplied to a clock terminal of an initial-stage flip-flop according to the count mode, wherein the counter clock input to the initial-stage clock switch is used as a least significant bit of a count value.

4. An analog-to-digital conversion method for converting a difference signal component into digital data, the difference signal component representing a difference between a reference component and a signal component included in an analog signal subject to processing, the method being carried out using an asynchronous counter circuit that is allowed to selectively perform counting in an up-count mode or counting in a down-count mode and comprising the steps of:
in a first processing iteration, comparing a signal corresponding to one of the reference component and the signal component with a reference signal for conversion into digital data, and, concurrently with the comparison, counting in one of the down-count mode and the up-count mode based on a counter clock and holding a count value at a time of completion of the comparison; and
in a second processing iteration, comparing the other one of the reference component and the signal component with the reference signal, and, concurrently with the comparison, counting in the other one of the down-count mode and the up-count mode and holding a count value at a time of completion of the comparison,
wherein,
the counter is configured so that when switching between the count modes occurs, a running count value is broken and there is an interval between count modes and when a mode begins the running count value is reset to the value before the running count value was broken.

5. The analog-to-digital conversion method according to claim 4, wherein the counting in the down-count mode and the up-count mode is performed using a common up/down counter while switching processing mode of the up/down counter.

6. The analog-to-digital conversion method according to claim 4 wherein the counting in the second processing iteration is staffed from the count value held in the first processing iteration.

7. The analog-to-digital conversion method according to claim 4, wherein the reference signal is caused to have the same changing characteristics between the first processing iteration and the second processing iteration.

8. The analog-to-digital conversion method according to claim 4, wherein the count value held in the second processing iteration for a previous signal subject to processing is stored in a data storage unit, and when the first processing iteration and the second processing iteration are performed for a current signal subject to processing, the count value is read concurrently from the data storage unit.

9. The analog-to-digital conversion method according to claim 4, wherein the signal subject to processing is an analog unit signal that is generated by a unit-signal generator and output in a column direction in a semiconductor device for detecting a distribution of physical quantities, the semiconductor device including a matrix of unit elements, each of the unit elements including a charge generator that generates charges corresponding to incident electromagnetic wave and including the unit-signal generator that generates a unit signal corresponding to the charges generated by the charge generator.

10. The analog-to-digital conversion method according to claim 9, wherein the analog unit signal generated by the unit-signal generator and output in the column direction is captured on a row-by-row basis, and the first processing iteration and the second processing iteration are performed for each of the unit elements on the row-by-row basis.

11. A solid state image device comprising:
an asynchronous counter circuit that is allowed to selectively perform counting in an up-count mode or counting in a down-count mode,
wherein,
the asynchronous counter includes a counter processor configured so that when switching between the count modes occurs, a running count value is broken and there is an interval between count modes and when a mode begins the running count value is reset to the value before the running count value was broken.

12. The solid state image device to claim 11, wherein a plurality of flip flops as basic elements of the counter is cascaded with each other, and said counter processor controls that clock terminals of said flip flops switches power supply level or ground level when said count value before switching of count mode are switched from count value converted by said count mode by said second control signal.

* * * * *